(12) United States Patent
Zhou et al.

(10) Patent No.: US 11,524,946 B2
(45) Date of Patent: Dec. 13, 2022

(54) POLYMERASE INHIBITORS AND RELATED COMPOSITIONS AND METHODS

(71) Applicant: Promega Corporation, Madison, WI (US)

(72) Inventors: Wenhui Zhou, Madison, WI (US); Kimberly K. Knoche, Madison, WI (US); Douglas R. Storts, Madison, WI (US); Min Zhou, Madison, WI (US); Poncho Meisenheimer, Madison, WI (US)

(73) Assignee: Promega Corporation, Madison, WI (US)

( * ) Notice: Subject to any disclaimer, the term of this patent is extended or adjusted under 35 U.S.C. 154(b) by 421 days.

(21) Appl. No.: 16/712,098

(22) Filed: Dec. 12, 2019

(65) Prior Publication Data

US 2020/0199088 A1   Jun. 25, 2020

Related U.S. Application Data

(60) Provisional application No. 62/778,590, filed on Dec. 12, 2018.

(51) Int. Cl.

| C07D 307/42 | (2006.01) |
| C07C 317/28 | (2006.01) |
| C07D 307/80 | (2006.01) |
| C07D 311/58 | (2006.01) |
| C12N 9/12   | (2006.01) |
| C12P 19/34  | (2006.01) |

(52) U.S. Cl.
CPC .......... *C07D 307/42* (2013.01); *C07C 317/28* (2013.01); *C07D 307/80* (2013.01); *C07D 311/58* (2013.01); *C12N 9/1252* (2013.01); *C12P 19/34* (2013.01); *C12Y 207/07007* (2013.01)

(58) Field of Classification Search
CPC .................................................. C07D 307/42
See application file for complete search history.

(56) References Cited

FOREIGN PATENT DOCUMENTS

WO    WO 2009/048611 A2    4/2009

OTHER PUBLICATIONS

Chakrabarti et al., "The enhancement of PCR amplification by low molecular weight amides," Nucleic Acids Research 29(11), 2001, 2377-2381.
Int'l Search Report and Written Opinion of the ISA for PCT/US2019/065955, 12 pages.
Saiki et al., "Primer-Directed Enzymatic Amplification of DNA with a Thermostable DNA Polymerase," Science 239(4839), 1988, 487-491.

*Primary Examiner* — Golam M Shameem
(74) *Attorney, Agent, or Firm* — Anne M. Reynolds; Casimir Jones, S.C.

(57) ABSTRACT

The present disclosure includes compositions and methods for improved DNA amplification reactions. In particular, the present disclosure provides compositions and methods for hot-start PCR applications using DNA polymerase inhibitors that minimize non-specific DNA amplification by inactivating DNA polymerase at lower temperatures.

11 Claims, 13 Drawing Sheets

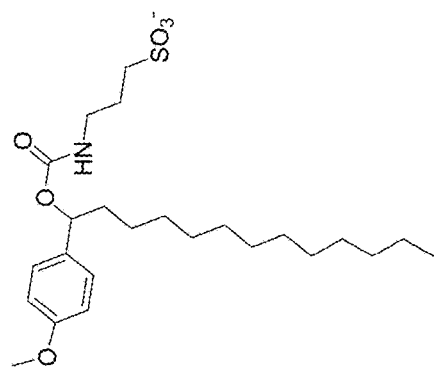
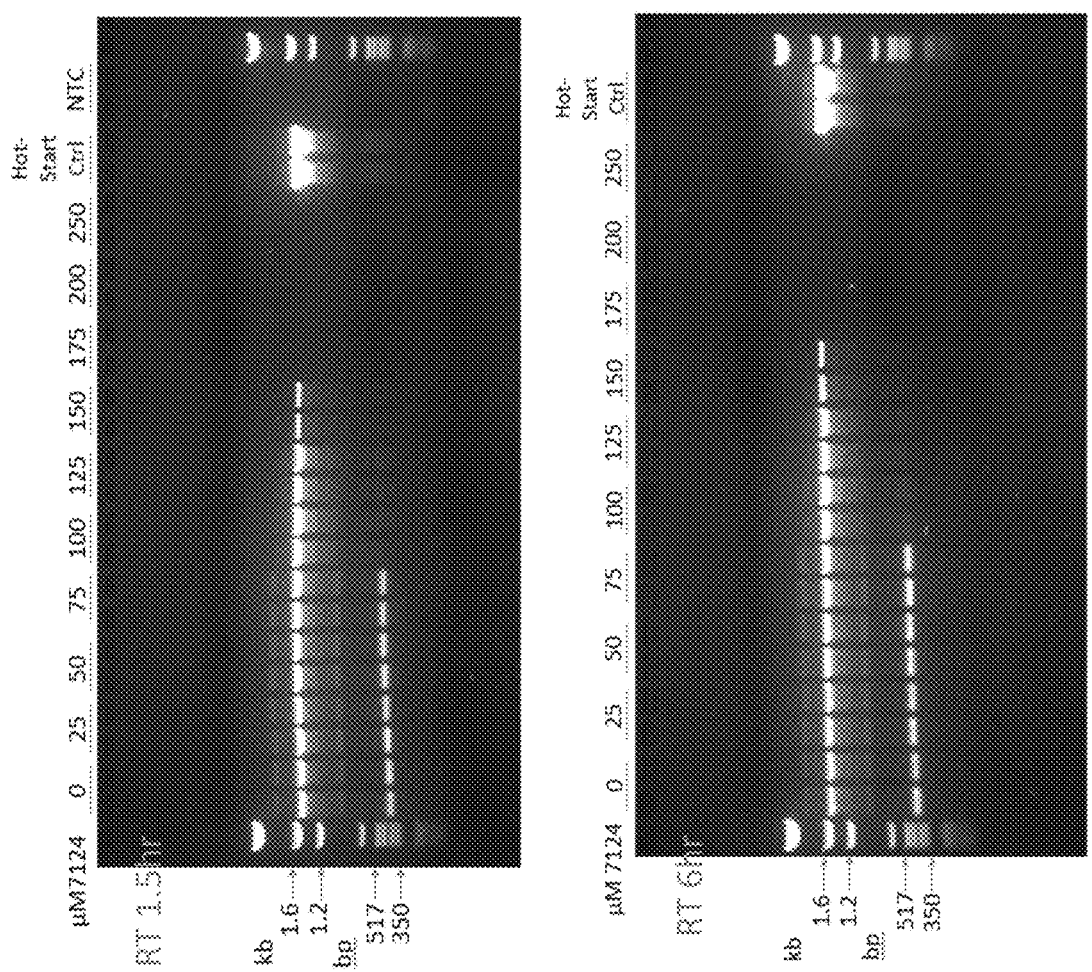
FIG. 1A

FIG. 1B
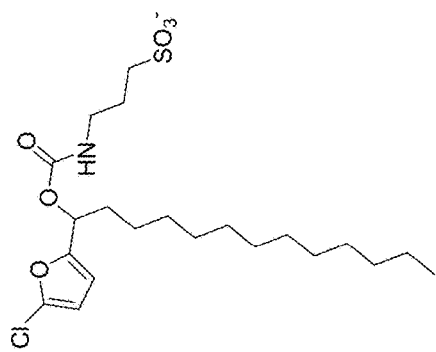
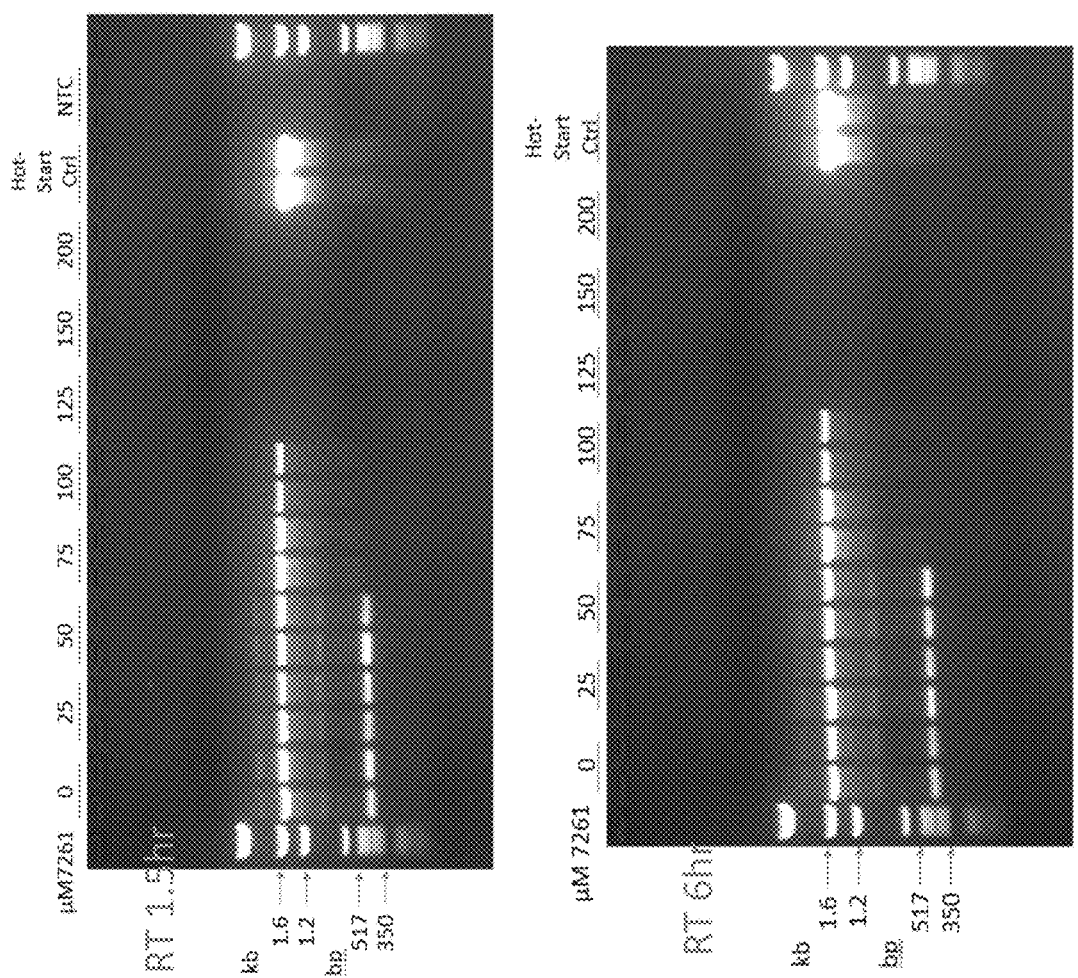

| Concentration | 7261 - SO3 | 7437 - COOH | 7438 - Asp #1 | 7438 - Asp #2 | 7439 - Glu #1 | 7439 - Glu #2 |
|---|---|---|---|---|---|---|
| 0µM | No HS (++) | No HS (++) | No HS (++) | No HS (++) | No HS (++) | No HS (++) |
| 1µM | | No HS (++) | No HS (++) | | No HS (++) | |
| 5µM | | No HS (++) | No HS (++) | | No HS (++) | |
| 10µM | | No HS (++) | No HS (++) | | No HS (++) | |
| 25µM | No HS (++) | No HS (++) | No HS (++) | HS (++) | No HS (++) | |
| 50µM | No HS (++) | No HS (++) | HS (+) | HS (++) | HS ? (++) | No HS (++) |
| 75µM | HS (++) | HS (+) | | HS (++) | | HS (++) |
| 100µM | HS (+) | | HS (low) | HS (++) | HS (++) | HS (++) |
| 125µM | No Amp | HS (low) | | HS (++) | | HS (++) |
| 150µM | No Amp | | | HS (++) | HS (+) | HS (++) |
| 175µM | | No Amp | No Amp | No Amp, HS (low) | HS (+) | HS (+) |
| 200µM | No Amp | | | | | HS (+) |
| 225µM | | | | | HS (low) | HS (low) |
| | Expt 090 | Expt 119 | Expt 120 | Expt 129 | Expt 121 | Expt 130 |

FIG. 2

| Concentration | 7489 - 1st | 2nd | 7490 - 1st | 2nd |
|---|---|---|---|---|
| 0μM | No HS (++) | No HS (++) | No HS (++) | No HS (++) |
| 1μM | No HS (++) | | No HS (++) | |
| 5μM | No HS (++) | | No HS (++) | |
| 10μM | No HS (++) | | No HS (++) | |
| 25μM | No HS (++) | No HS (++) | No HS (++) | |
| 50μM | No HS (++) | No HS (++) | No HS (++) | No HS (++) |
| 75μM | HS (++) | HS (++) | | No HS (++) |
| 100μM | | HS (++) | | HS (++) |
| 125μM | HS (+) | HS (+) | HS (+) | HS (+) |
| 150μM | | HS (low) | No Amp | |
| 175μM | | | | No Amp |
| 200μM | No Amp | No Amp | No Amp | No Amp |
| Expt | 137 | 146 | 138 | 147 |

| Concentration | 7487 - 1st | 2nd | 7488 - 1st | 2nd |
|---|---|---|---|---|
| 0μM | No HS (++) | No HS (++) | No HS (++) | No HS (++) |
| 1μM | No HS (++) | | No HS (++) | |
| 5μM | No HS (++) | | No HS (++) | |
| 10μM | No HS (++) | | No HS (++) | |
| 25μM | No HS (++) | No HS (++) | No HS (++) | |
| 50μM | No HS (++) | No HS (++) | No HS (++) | |
| 75μM | HS (++) | HS (++) | | No HS (++) |
| 100μM | HS (low) | HS (++) | HS ? (low) | HS (+) |
| 125μM | | HS (low) | | HS (+) |
| 150μM | No Amp | No Amp | No Amp | No Amp |
| 175μM | | No Amp | | No Amp |
| 200μM | | | | |
| Expt | 135 | 146 | 136 | 150 |

| Concentration | 7491 - 2nd | 3rd | 7493 - 1st | 2nd |
|---|---|---|---|---|
| 0μM | No HS (++) | No HS (++) | No HS (++) | No HS (++) |
| 1μM | | | No HS (++) | |
| 5μM | | | No HS (++) | |
| 10μM | No HS (++) | No HS (++) | No HS (++) | |
| 25μM | No HS (++) | No HS (++) | No HS (++) | |
| 50μM | No HS (++) | No HS (++) | No HS (++) | No HS (++) |
| 75μM | HS (++) | HS (++) | No HS (++) | No HS (++) |
| 100μM | No HS (++) | HS (+) | HS (++) | HS (+) |
| 125μM | HS (low) | HS (low) | No Amp | HS (+) |
| 150μM | No Amp | No Amp | No Amp | No Amp |
| 175μM | No Amp | No Amp | No Amp | |
| 200μM | | | | |
| Expt | 148 | 154 | 140 | 147 |

| Concentration | 7486 - 1st | 2nd | 7495 - 1st | 2nd |
|---|---|---|---|---|
| 0μM | No HS (++) | No HS (++) | No HS (++) | No HS (++) |
| 1μM | No HS (++) | | No HS (++) | |
| 5μM | No HS (++) | | No HS (++) | |
| 10μM | No HS (++) | | No HS (++) | |
| 25μM | No HS (++) | | No HS (++) | No HS (++) |
| 50μM | No HS (++) | | HS (++) | HS (+) |
| 75μM | No HS (++) | No HS (++) | No Amp | No Amp |
| 100μM | HS (+)? | HS (+) | No Amp | No Amp |
| 125μM | | HS (low)? | | No Amp |
| 150μM | No Amp | No Amp | No Amp | |
| 175μM | | No Amp | | |
| 200μM | | | No Amp | |
| 225μM | | | | |
| Expt | 143 | 153 | 144 | 149 |

| Compound | Detergent 22°C IC$_{50}$ Range |
|---|---|
| 7124 | 100 – 200uM (IC$_{50}$ about 150uM) |
| 7126 | 1.0 – 1.5mM (IC$_{50}$ between 1.0 – 1.25mM) |
| 7127 | 400 – 800uM (IC$_{50}$ about 600uM) |
| 7123 | 100 – 200uM (IC$_{50}$ about 100uM) |
| 7125 | No activity seen |
| 6966 | 1.25 – 2.0mM (IC$_{50}$ about 1.25mM) |
| SDS | 100 – 200uM (IC$_{50}$ about 150uM) |

POLYMERASE INHIBITORS AND RELATED COMPOSITIONS AND METHODS

CROSS-REFERENCE TO RELATED APPLICATIONS

This application claims priority to U.S. Provisional Patent Application No. 62/778,590, filed on Dec. 12, 2018, the entire contents of which are fully incorporated herein by reference.

FIELD

Provided herein are compositions and methods for improved DNA amplification reactions. In particular, the present disclosure provides compositions and methods for hot-start PCR applications using DNA polymerase inhibitors that minimize non-specific DNA amplification by inactivating DNA polymerase at lower temperatures.

BACKGROUND

Biological PCR is a rapid and simple method for specifically amplifying a target DNA sequence in an exponential manner (e.g., Saiki, et al., *Science* 239:487-4391 (1988); herein incorporated by reference in its entirety). Polymerase chain reaction (PCR) is a technology in molecular biology used to amplify a single copy or a few copies of a piece of DNA across several orders of magnitude, generating thousands to millions of copies of a particular DNA sequence. Hot-start PCR is a modified form of polymerase chain reaction (PCR) that avoids a non-specific amplification of DNA by inactivating the DNA polymerase at lower temperatures. Initially, hot-start PCR was performed by withholding the $Mg^{2+}$, dNTP, or enzyme until immediately before initial denaturation during cycling begins. Alternatively, hot-start PCR can be achieved by separating the reaction components with a wax bead barrier that melts as the mixture is heated during the initial denaturation step of the PCR.

Other hot-start PCR methodologies include the use of specific antibodies or reversible chemical modifications of the polymerase (e.g., modifications of the lysine with organic acid anhydride) to block the activity of the DNA polymerase at lower temperature. An initial activation step at 95° C. is therefore required for activation of the polymerase. This step will both denature antibodies linked to the active center of the enzyme and also remove any lysine modifications, made with acid anhydride, from the chemically modified DNA polymerase. For example, anti-Taq antibodies reduce Taq polymerase activity below 72° C., the optimal temperature at which the enzyme extends the primers. When the specific antibodies detach from Taq-polymerase, the amplification proceeds with greater specificity.

However, there are significant disadvantages of using antibody-based hot-start PCR or hot-start PCR based on chemical modifications of the DNA polymerase. For example, antibody-based hot-start PCR requires the use of a different antibody for each enzyme used in a PCR reaction, and chemical modifications to the DNA polymerase can require longer times at 95° C. to activate the enzymes and not all enzyme activity may be recovered.

SUMMARY

Provided herein are compounds of formula (I):

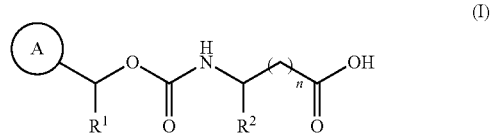

or a salt thereof, wherein:

A is selected from aryl, heteroaryl, and heterocyclyl, each of which may be optionally substituted with 1, 2, or 3 substituents;

$R^1$ is $C_6$-$C_{20}$ alkyl;

$R^2$ is selected from hydrogen and —COOH; and n is 1 or 2.

In some embodiments, A is phenyl that is unsubstituted or substituted with 1, 2, 3, or 4 substituents independently selected from $C_1$-$C_4$ alkyl, $C_1$-$C_4$ alkoxy, and halo. In some embodiments, A is a 5- or 6-membered monocyclic heteroaryl that is unsubstituted or substituted with 1, 2, or 3 substituents independently selected from $C_1$-$C_4$ alkyl, $C_1$-$C_4$ alkoxy, and halo. In some embodiments, A is a bicyclic heterocyclyl group that is unsubstituted. In some embodiments, A is selected from 2,3-dihydrobenzofuranyl and chromanyl.

In some embodiments, $R^1$ is $C_8$-$C_{14}$ alkyl. In some embodiments, $R^1$ is $C_{12}$ alkyl.

In some embodiments, $R^2$ is hydrogen. In some embodiments, $R^2$ is —COOH.

In some embodiments, n is 1. In some embodiments, n is 2.

In some embodiments, the compound is in the form of an alkali metal salt.

In some embodiments, the compound is selected from:

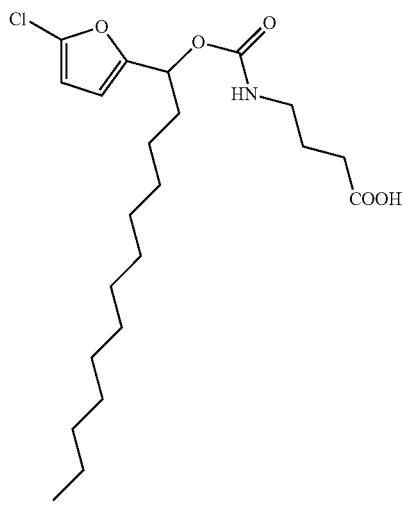

3
-continued
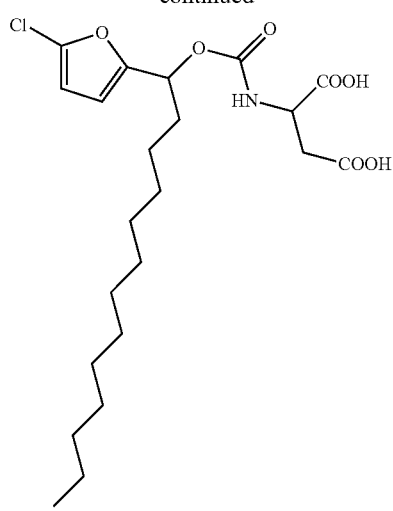
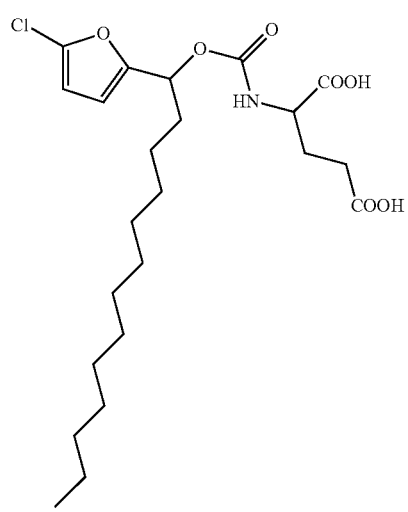
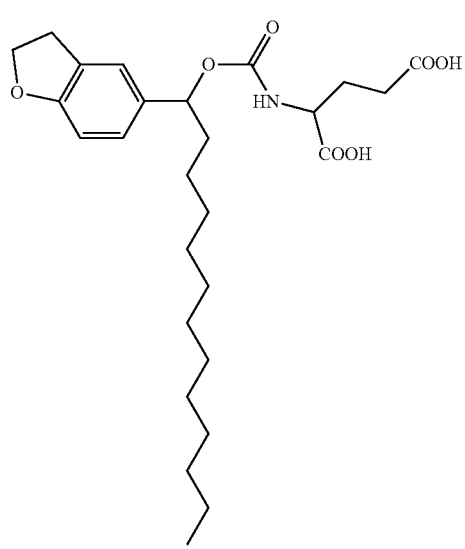
4
-continued
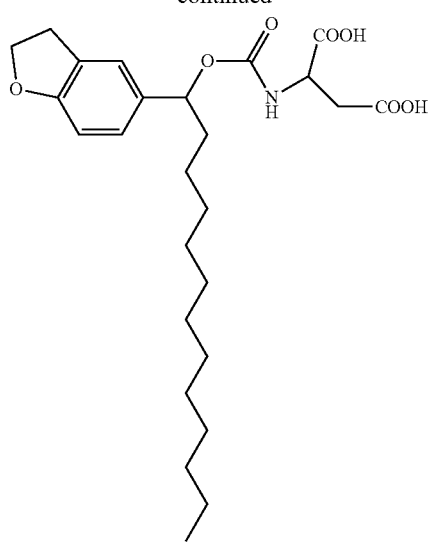
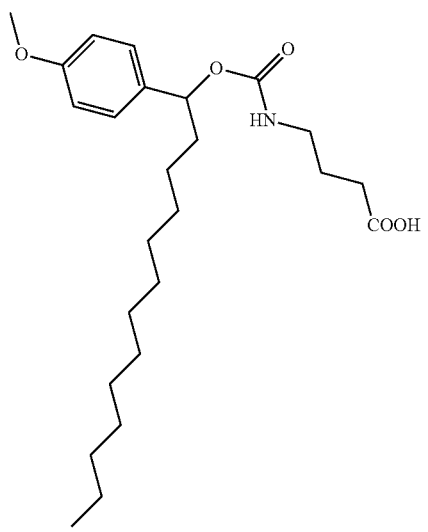
and
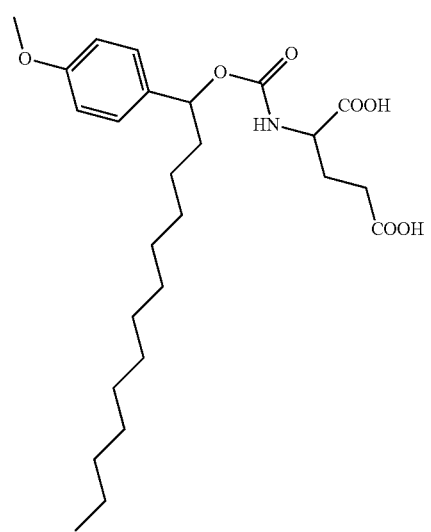

-continued

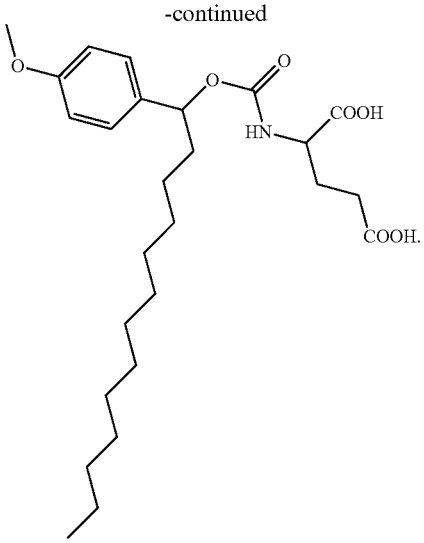

Provided herein are compositions comprising a compound of formula (I) as described herein, and a DNA polymerase. In some embodiments, the DNA polymerase is a thermostable DNA polymerase. In some embodiments, the thermostable DNA polymerase is selected from the group consisting of: Taq, Tca, Tfu, Tbr, Tth, Tih, Tfi, Tli, Tfl, Pfu, Pwo, KOD, Tma, Tne, Bst, Pho, Sac, Sso, ES4, or a mutant, variant, or derivative thereof. In some embodiments, the compound is bound to the DNA polymerase. In some embodiments, the compound inhibits the activity of the DNA polymerase.

In some embodiments, the composition comprises one or more nucleic acid amplification reagents. In some embodiments, the one or more amplification reagents are selected from the group consisting of: deoxynucleotide triphosphates, buffer, a magnesium salt (e.g., $MgCl_2$ or $MgSO_4$), an oligonucleotide primer, and a nucleic acid template.

Provided herein are compositions comprising a compound of formula (I) as described herein, and one or more nucleic acid amplification reagents. In some embodiments, the one or more amplification reagents are selected from the group consisting of: a polymerase, deoxynucleotide triphosphates, buffer, a magnesium salt (e.g., $MgCl_2$ or $MgSO_4$), an oligonucleotide primer, and a nucleic acid template.

Provided herein are compositions comprising a compound of formula (II):

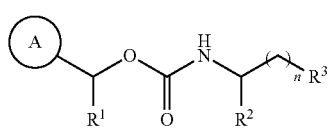

(II)

or a salt thereof,
wherein:
A is selected from a monocyclic or bicyclic aryl, heteroaryl, or heterocyclyl group, each of which may be optionally substituted with 1, 2, or 3 substituents;
$R^1$ is $C_6$-$C_{20}$ alkyl;
$R^2$ is selected from hydrogen and —COOH;
n is 1 or 2; and
$R^3$ is selected from —COOH and —$SO_3X$, wherein X is selected from hydrogen, an alkali metal cation, and an ammonium cation; and
one or more nucleic acid amplification reagents.

In some embodiments, A is phenyl that is unsubstituted or substituted with 1, 2, 3, or 4 substituents independently selected from $C_1$-$C_4$ alkyl, $C_1$-$C_4$ alkoxy, and halo. In some embodiments, A is a 5- or 6-membered monocyclic heteroaryl that is unsubstituted or substituted with 1, 2, or 3 substituents independently selected from $C_1$-$C_4$ alkyl, $C_1$-$C_4$ alkoxy, and halo. In some embodiments, A is a bicyclic heterocyclyl group that is unsubstituted. In some embodiments, A is selected from 2,3-dihydrobenzofuranyl and chromanyl.

In some embodiments, $R^1$ is $C_8$-$C_{14}$ alkyl. In some embodiments, $R_1$ is $C_{12}$ alkyl.

In some embodiments, $R^2$ is hydrogen. In some embodiments, $R^2$ is —COOH.

In some embodiments, n is 1. In some embodiments, n is 2.

In some embodiments, $R^3$ is —COOH. In some embodiments, $R^3$ is —$SO_3X$, and X is a sodium cation.

In some embodiments, the compound is in the form of an alkali metal salt.

In some embodiments, compound of formula (II) is selected from:

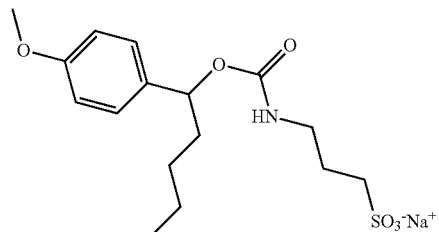

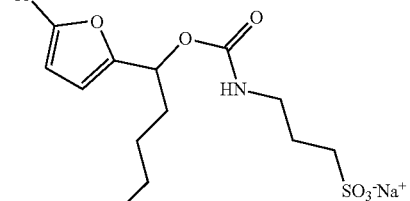

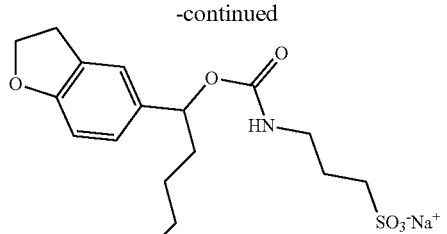
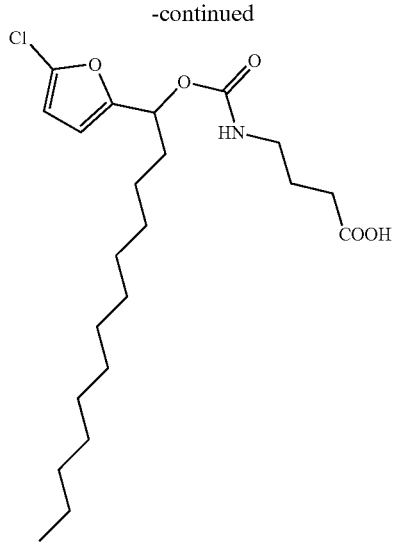
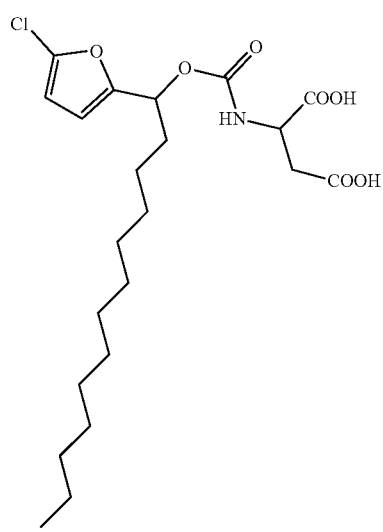
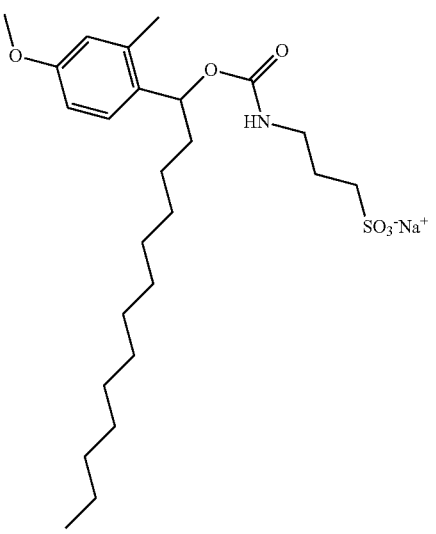

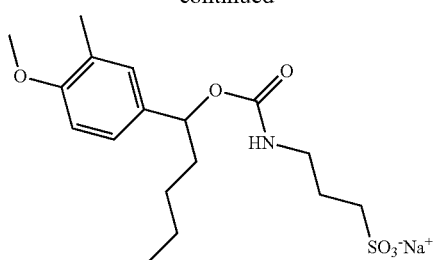
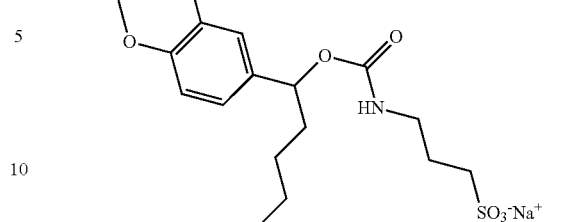
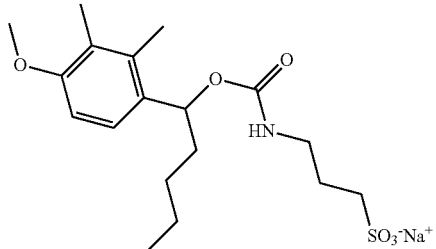
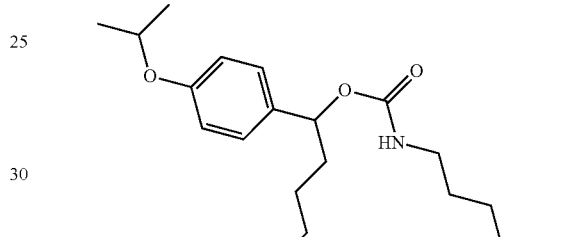
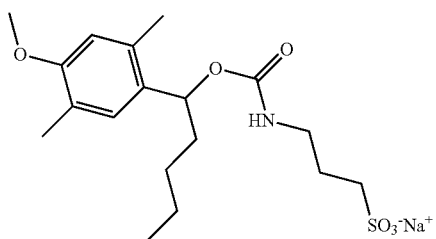
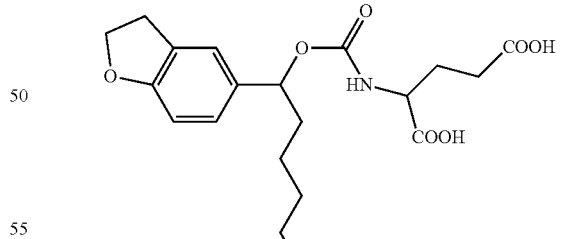
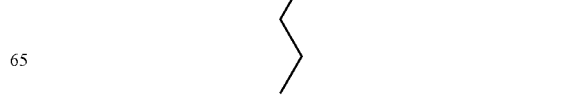

11 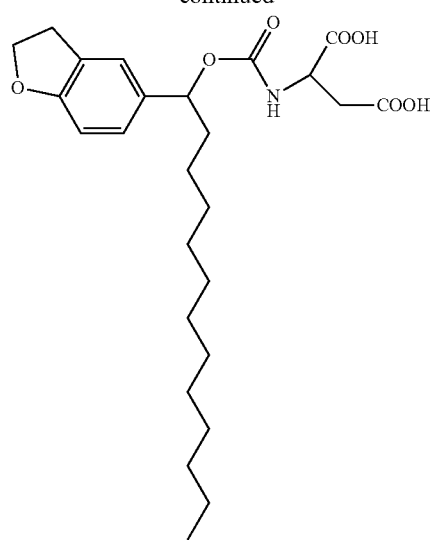 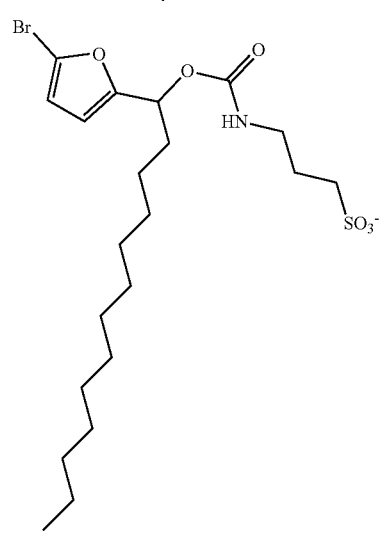
12 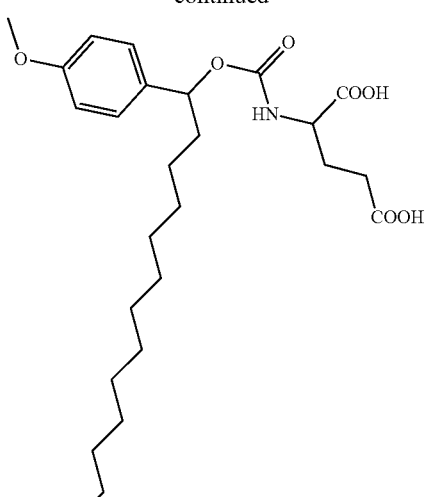 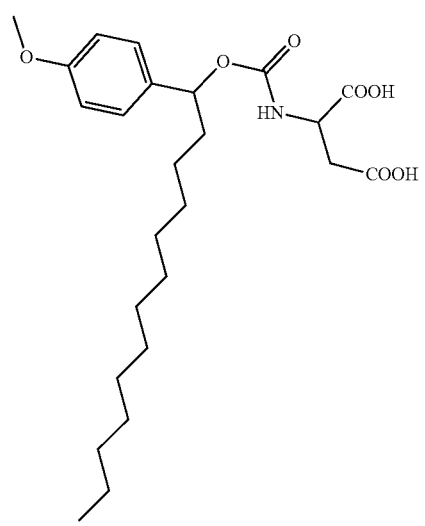 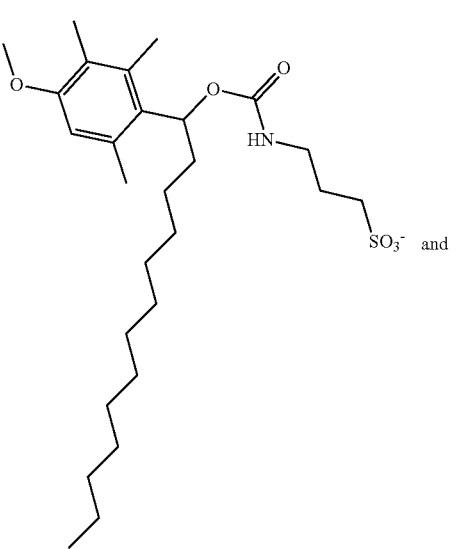 and

-continued

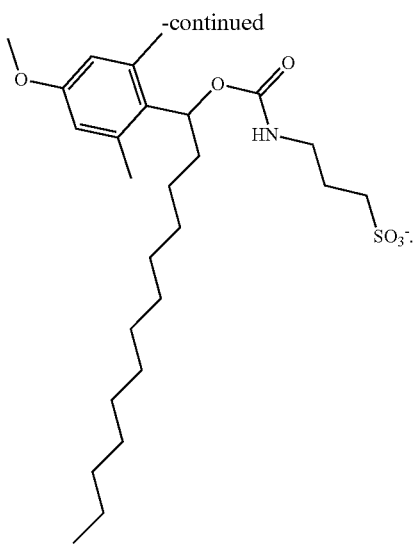

In some embodiments, the one or more amplification reagents are selected from the group consisting of: a polymerase, deoxynucleotide triphosphates, buffer, a magnesium salt (e.g., $MgCl_2$ or $MgSO_4$), an oligonucleotide primer, and a nucleic acid template.

Provided herein are methods of temperature-dependent inhibition of polymerase activity comprising contacting a DNA polymerase with a compound of formula (II):

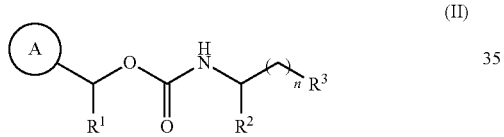

(II)

or a salt thereof,
wherein:
A is selected from a monocyclic or bicyclic aryl, heteroaryl, or heterocyclyl group, each of which may be optionally substituted with 1, 2, or 3 substituents;
$R^1$ is $C_6$-$C_{20}$ alkyl;
$R^2$ is selected from hydrogen and —COOH;
n is 1 or 2; and
$R^3$ is selected from —COOH and —$SO_3X$, wherein X is selected from hydrogen, an alkali metal cation, and an ammonium cation.

In some embodiments, A is phenyl that is unsubstituted or substituted with 1, 2, 3, or 4 substituents independently selected from $C_1$-$C_4$ alkyl, $C_1$-$C_4$ alkoxy, and halo. In some embodiments, A is a 5- or 6-membered monocyclic heteroaryl that is unsubstituted or substituted with 1, 2, or 3 substituents independently selected from $C_1$-$C_4$ alkyl, $C_1$-$C_4$ alkoxy, and halo. In some embodiments, A is a bicyclic heterocyclyl group that is unsubstituted. In some embodiments, A is selected from 2,3-dihydrobenzofuranyl and chromanyl.

In some embodiments, $R^1$ is $C_8$-$C_{14}$ alkyl. In some embodiments, $R_1$ is $C_{12}$ alkyl.

In some embodiments, $R^2$ is hydrogen. In some embodiments, $R^2$ is —COOH.

In some embodiments, n is 1. In some embodiments, n is 2.

In some embodiments, $R^3$ is —COOH. In some embodiments, $R^3$ is —$SO_3X$, wherein X is a sodium cation.

In some embodiments, the compound of formula (II) is selected from:

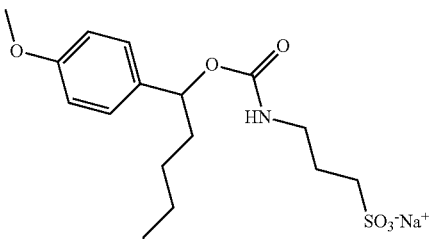

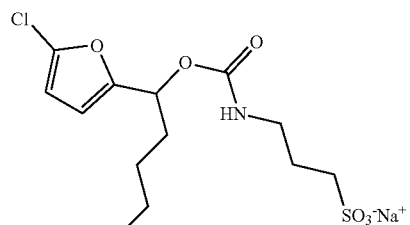

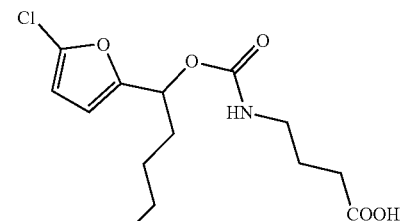

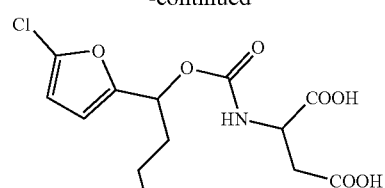
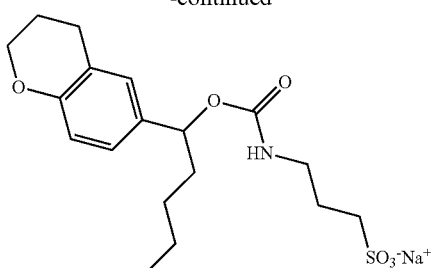
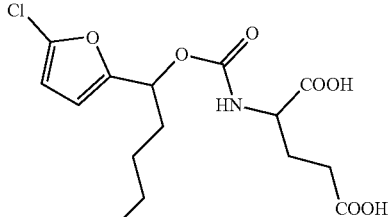
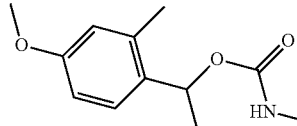
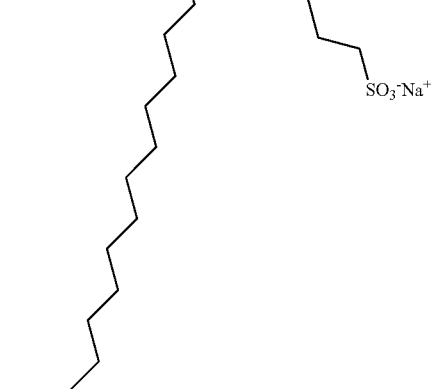
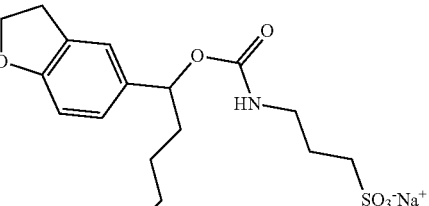
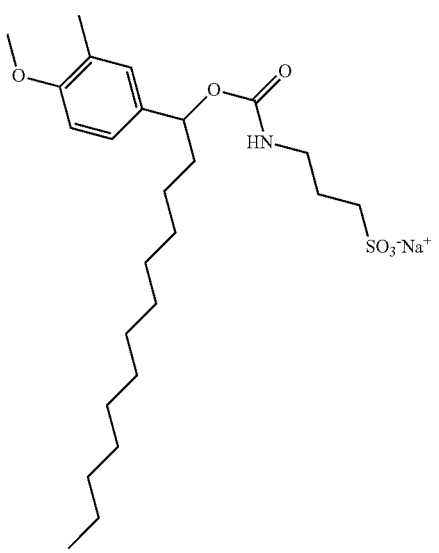

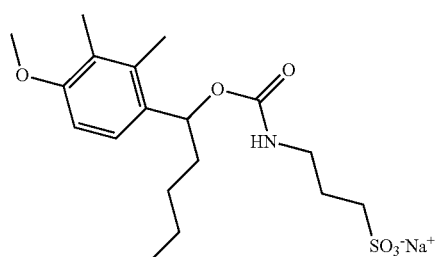
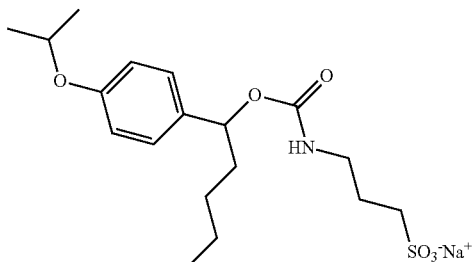
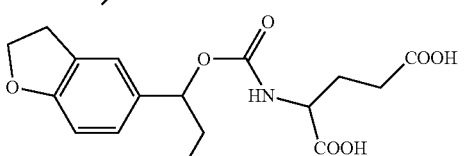
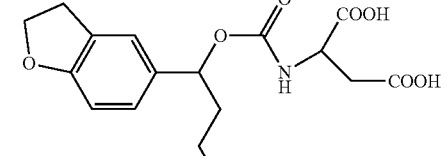

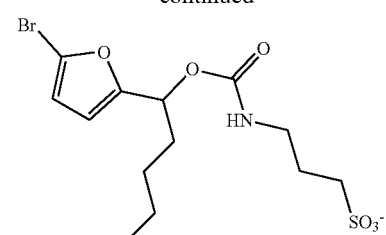
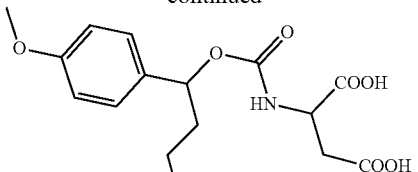
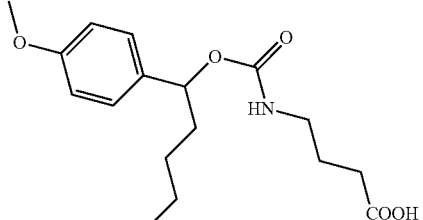
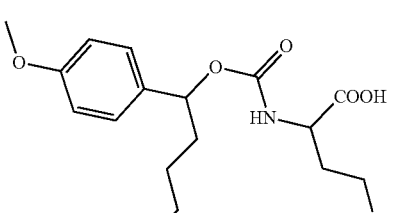
and
In some embodiments, the polymerase is a thermostable DNA polymerase. In some embodiments, the thermostable DNA polymerase is selected from the group consisting of: Taq, Tca, Tfu, Tbr, Tth, Tih, Tfi, Tli, Tfl, Pfu, Pwo, KOD, Tma, Tne, Bst, Pho, Sac, Sso, ES4, or a mutant, variant, or derivative thereof.

Provided herein are methods of activating an inhibited polymerase comprising exposing a DNA polymerase inhibited by a compound of formula (II):

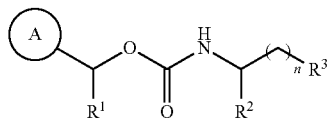

(II)

or a salt thereof,
wherein:
A is selected from a monocyclic or bicyclic aryl, heteroaryl, or heterocyclyl group, each of which may be optionally substituted with 1, 2, or 3 substituents;
$R^1$ is $C_6$-$C_{20}$ alkyl;
$R^2$ is selected from hydrogen and —COOH;
n is 1 or 2; and
$R^3$ is selected from —COOH and —$SO_3$X, wherein X is selected from hydrogen, an alkali metal cation, and an ammonium cation; and
heating to a temperature above 80° C. to activate the DNA polymerase.

In some embodiments, the compound is a compound of formula (I):

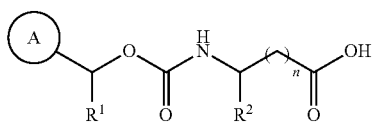

(I)

or a salt thereof,
wherein:
A is selected from aryl, heteroaryl, and heterocyclyl, each of which may be optionally substituted with 1, 2, or 3 substituents;
$R^1$ is $C_6$-$C_{20}$ alkyl;
$R^2$ is selected from hydrogen and —COOH; and
n is 1 or 2.

In some embodiments, the polymerase is a thermostable DNA polymerase. In some embodiments, the thermostable DNA polymerase is selected from the group consisting of: Taq, Tca, Tfu, Tbr, Tth, Tih, Tfi, Tli, Tfl, Pfu, Pwo, KOD, Tma, Tne, Bst, Pho, Sac, Sso, ES4, or a mutant, variant, or derivative thereof. In some embodiments, the temperature is above 90° C.

Provided herein are methods of amplifying a nucleic acid comprising:
(a) adding amplification reagents and a nucleic acid template to a DNA polymerase inhibited by a compound of formula (II):

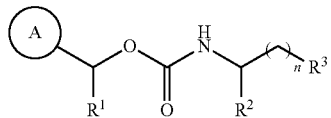

(II)

or a salt thereof,
wherein:
A is selected from a monocyclic or bicyclic aryl, heteroaryl, or heterocyclyl group, each of which may be optionally substituted with 1, 2, or 3 substituents;
$R^1$ is $C_6$-$C_{20}$ alkyl;
$R^2$ is selected from hydrogen and —COOH;
n is 1 or 2; and
$R^3$ is selected from —COOH and —$SO_3$X, wherein X is selected from hydrogen, an alkali metal cation, and an ammonium cation;
(b) heating to a temperature of at least 80° C. to activate the DNA polymerase; and
(c) running through a thermal cycling protocol of appropriate times and temperatures for the amplification reagents and a nucleic acid template.

In some embodiments, the amplification reagents comprise: deoxynucleotide triphosphates, buffer, a magnesium salt (e.g., $MgCl_2$ or $MgSO_4$), and an oligonucleotide primer. In some embodiments, the amplification reagents comprise forward and reverse primers for a target on the nucleic acid template. In some embodiments, the DNA polymerase is activated by heating to a temperature above 80° C. In some embodiments, the thermal cycling protocol comprises a three temperature cycle of (i) a high temperature denaturation step, (ii) a low temperature annealing step, and (iii) a middle temperature extension step, repeated 5 or more times in succession. In some embodiments, the denaturation, annealing, and extension steps are repeated 20 or more times in succession. In some embodiments, the thermal cycling protocol comprises a two temperature cycle of a high temperature denaturation step, a middle/low temperature annealing/extension step repeated 5 or more times in succession. In some embodiments, the denaturation and annealing/extension steps are repeated 20 or more times in succession.

BRIEF DESCRIPTION OF THE DRAWINGS

FIGS. 1A-1B include representative images of agarose gels used to evaluate the amplification products of various hot-start PCR reactions performed with and without two different polymerase inhibitors (compound #7124 in FIG. 1A; compound #7261 in FIG. 1B).

FIG. 2 includes a representative table of the results of various hot-start PCR reactions performed with different polymerase inhibitors (i.e., compound #7437, compound #7438, and compound #7439; variations of compound #7261).

FIG. 8 includes a representative table of results of $IC_{50}$ values for different polymerase inhibitors (i.e. compound #7124, compound #7126, compound #7127, compound #7123, compound #7125, compound #6966, and SDS).

FIG. 9 includes a representative table of the results of various hot-start PCR reactions performed with polymerase inhibitor compound #7124 and polymerase enzyme at the various concentrations shown.

FIG. 10 includes a representative table of the results of various hot-start PCR reactions performed with polymerase inhibitor compound #7261 and polymerase enzyme at the various concentrations shown.

DETAILED DESCRIPTION

Figure 3:
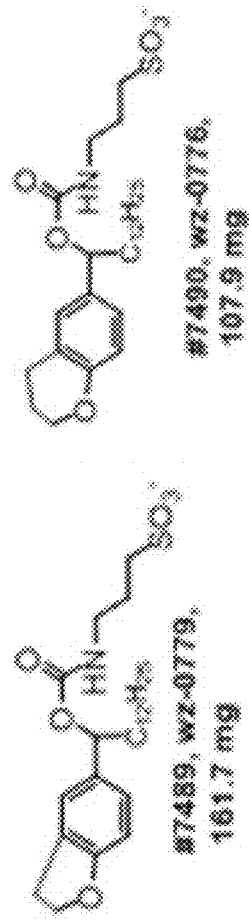
FIG. 3 includes a representative table of the results of various hot-start PCR reactions performed with different polymerase inhibitors (i.e., compound #7489 and compound #7490; variations of compound #7124).

Provided herein are compositions and methods for improved DNA amplification reactions. In particular, the present disclosure provides compositions and methods for hot-start PCR applications using DNA polymerase inhibitors that minimize non-specific DNA amplification by inactivating DNA polymerase at lower temperatures.

Embodiments of the present disclosure provide novel thermally-labile small molecule polymerase inhibitors for PCR applications (e.g., hot-start PCR). The addition of thermally-labile molecules to amplification reactions provides improved hot-start PCR applications by inhibiting DNA polymerase activity at lower temperatures. Unlike antibody-based hot-start PCR, use of a thermally-labile small molecule polymerase inhibitor is a simple and universal approach widely applicable to different DNA polymerases that may be used in hot-start PCR applications. Embodiments provided herein also eliminate undesired nuclease activity associated with DNA polymerases and avoid non-specific product amplification at low temperatures, thus producing an amplified product with higher specificity and yield.

As would be recognized by one of ordinary skill in the art based on the present disclosure, many challenging PCR reactions and analyses benefit from a hot start, and in some cases, a hot start is required to amplify a desired DNA target. This includes reactions which have very low copy numbers of target (e.g., 1 HIV genome per 10,000 cells), denatured DNA (e.g., many DNA extraction procedures include a boiling step so that the template is single-stranded during reaction setup), or contaminated DNA (e.g., DNA from soil or feces and/or DNA containing large amounts of RNA). Additionally, other challenges that can be addressed with hot-start PCR include poorly designed primers, multiplexing amplifications into single reactions, and having similar (but not identical) target sites in the DNA template. The novel thermally-labile small molecule DNA polymerase inhibitors of the present disclosure address these challenges.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents, and other references mentioned herein are incorporated by reference in their entirety. The materials, methods, and examples disclosed herein are illustrative only and not intended to be limiting.

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Sorrell, Organic Chemistry, $2^{nd}$ edition, University Science Books, Sausalito, 2006; Smith, March's Advanced Organic Chemistry: Reactions, Mechanism, and Structure, $7^{th}$ Edition, John Wiley & Sons, Inc., New York, 2013; Larock, Comprehensive Organic Transformations, $3^{rd}$ Edition, John Wiley & Sons, Inc., New York, 2018; Carruthers, Some Modern Methods of Organic Synthesis, $3^{rd}$ Edition, Cambridge University Press, Cambridge, 1987; the entire contents of each of which are incorporated herein by reference.

The term "alkoxy", as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl", as used herein, means a straight or branched saturated hydrocarbon chain containing from 1 to 30 carbon atoms, for example 1 to 16 carbon atoms ($C_1$-$C_{16}$ alkyl), 1 to 14 carbon atoms ($C_1$-$C_{14}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_8$ alkyl), 1 to 6 carbon atoms ($C_1$-$C_6$ alkyl), 1 to 4 carbon atoms ($C_1$-$C_4$ alkyl), 6 to 20 carbon atoms ($C_6$-$C_{20}$ alkyl), or 8 to 14 carbon atoms ($C_8$-$C_{14}$ alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

The term "alkenyl", as used herein, refers to a straight or branched hydrocarbon chain containing from 2 to 30 carbon atoms and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl", as used herein, refers to a straight or branched hydrocarbon chain containing from 2 to 30 carbon atoms and containing at least one carbon-carbon triple bond. Representative examples of alkynyl include, but are not limited to, ethynyl, propynyl, and butynyl.

The term "aryl", as used herein, refers to a phenyl group, or a bicyclic or tricyclic aromatic fused ring system. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl.

The term "cycloalkyl", as used herein, refers to a saturated carbocyclic ring system containing three to ten carbon atoms and zero heteroatoms. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, bicyclo[2.2.1]heptanyl, bicyclo[3.2.1]octanyl, and bicyclo[5.2.0]nonanyl.

The term "cycloalkenyl", as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "halogen" or "halo", as used herein, means F, Cl, Br, or I.

The term "haloalkyl", as used herein, means an alkyl group, as defined herein, in which one, two, three, four, five, six, seven or eight hydrogen atoms are replaced by a halogen.

The term "heteroaryl", as used herein, refers to an aromatic monocyclic ring or an aromatic bicyclic ring system or an aromatic tricyclic ring system. The aromatic monocyclic rings are five- or six-membered rings containing at least one heteroatom independently selected from the group consisting of N, O, and S (e.g. 1, 2, 3, or 4 heteroatoms independently selected from 0, S, and N). The five-membered aromatic monocyclic rings have two double bonds, and the six-membered aromatic monocyclic rings have three double bonds. The bicyclic heteroaryl groups are exemplified by a monocyclic heteroaryl ring appended fused to a monocyclic aryl group, as defined herein, or a monocyclic, heteroaryl group, as defined herein. The tricyclic heteroaryl groups are exemplified by a monocyclic heteroaryl ring fused to two rings independently selected from a monocyclic aryl group, as defined herein or a monocyclic heteroaryl group as defined herein. Representative examples of monocyclic heteroaryl include, but are not limited to, pyridinyl (including pyridin-2-yl, pyridin-3-yl, pyridin-4-yl), pyrimidinyl, pyrazinyl, pyridazinyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, furanyl, oxazolyl, isoxazolyl, 1,2,4-triazinyl, and 1,3,5-triazinyl. Representative examples of bicyclic heteroaryl include, but are not limited to, benzimidazolyl, benzodioxolyl, benzofuranyl, benzooxadiazolyl, benzopyrazolyl, benzothiazolyl, benzothienyl, benzotriazolyl, benzoxadiazolyl, benzoxazolyl, chromenyl, imidazopyridine, imidazothiazolyl, indazolyl, indolyl, isobenzofuranyl, isoindolyl, isoquinolinyl, naphthyridinyl, purinyl, pyridoimidazolyl, quinazolinyl, quinolinyl, quinoxalinyl, thiazolopyridinyl, thiazolopyrimidinyl, thienopyrrolyl, and thienothienyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings.

The term "heterocycle" or "heterocyclic", as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings.

The term "hydroxy", as used herein, means an —OH group.

In some instances, the number of carbon atoms in a group (e.g., alkyl, alkoxy, or cycloalkyl) is indicated by the prefix "$C_x$-$C_y$-", wherein x is the minimum and y is the maximum number of carbon atoms in the group. Thus, for example, "$C_1$-$C_3$-alkyl" refers to an alkyl group containing from 1 to 3 carbon atoms.

The term "substituent" refers to a group substituted on an atom of the indicated group.

When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable group known to those of skill in the art (e.g., one or more of the groups recited below). Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkyl sulfonyl, aryl sulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The terms "comprise(s)", "include(s)", "having", "has", "can", "contain(s)", and variants thereof, as used herein, are intended to be open-ended transitional phrases, terms, or words that do not preclude the possibility of additional acts or structures. The singular forms "a", "and", and "the" include plural references unless the context clearly dictates otherwise. Many embodiments herein are described using open "comprising" language. Such embodiments encompass multiple closed "consisting of" and/or "consisting essentially of" embodiments, which may alternatively be claimed or described using such language. The present disclosure also contemplates other embodiments "comprising", "consisting of", and "consisting essentially of" the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Isolated polynucleotide" as used herein may mean a polynucleotide (e.g., of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

"Peptide" and "polypeptide", as used herein, and unless otherwise specified, refer to polymer compounds of two or more amino acids joined through the main chain by peptide amide bonds (—C(O)NH—). The term "peptide" typically refers to short amino acid polymers (e.g., chains having fewer than 25 amino acids), whereas the term "polypeptide" typically refers to longer amino acid polymers (e.g., chains having more than 25 amino acids).

"Sample", "test sample", "specimen", "sample from a subject", and "patient sample" as used herein may be used interchangeable and may be a sample of blood, such as whole blood, tissue, urine, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Sequence identity" refers to the degree two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families, e.g., acidic (e.g., aspartate, glutamate), basic (e.g., lysine, arginine, histidine), non-polar (e.g., alanine, valine, leucine, isoleucine, proline, phenylalanine, methionine, tryptophan), and uncharged polar (e.g., glycine, asparagine, glutamine, cysteine, serine, threonine, tyrosine). The "percent sequence identity" (or "percent sequence similarity") is calculated by: (1) comparing two optimally aligned sequences over a window of comparison (e.g., the length of the longer sequence, the length of the shorter sequence, a specified window), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

"Subsequence" refers to peptide or polypeptide that has 100% sequence identify with another, larger peptide or polypeptide. The subsequence is a perfect sequence match for a portion of the larger amino acid chain.

"Substantially", as used herein, means that the recited characteristic, parameter, and/or value need not be achieved exactly, but that deviations or variations, including for example, tolerances, measurement error, measurement accuracy limitations, and other factors known to skill in the art, may occur in amounts that do not preclude the effect the characteristic was intended to provide. A characteristic or feature that is substantially absent be one that is within the noise, beneath background, below the detection capabilities of the assay being used, or a small fraction (e.g., <1%, <0.1%, <0.01%, <0.001%, <0.00001%, <0.000001%, <0.0000001%) of the significant characteristic.

"Variant" is used herein to describe a peptide or polypeptide that differs in amino acid sequence by the insertion, deletion, or conservative substitution of amino acids, but retain at least one biological activity. "SNP" refers to a variant that is a single nucleotide polymorphism. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid (e.g., replacing an amino acid with a different amino acid of similar properties, such as hydrophilicity, degree, and distribution of charged regions) is recognized in the art as typically involving a minor change. These minor changes can be identified, in part, by considering the hydropathic index of amino acids, as understood in the art. The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. DNA POLYMERASE INHIBITORS

The present disclosure includes materials and methods related to hot-start PCR using novel thermally-labile small molecule DNA polymerase inhibitors. In accordance with these embodiments, the present disclosure includes DNA polymerase inhibitors comprising a carbon chain tail ($R^1$), a core group (A) that allows for breakdown of the molecule, and a head group.

In some embodiments, the disclosure provides a compound of formula (I):

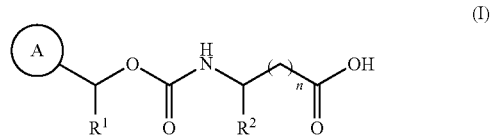

or a salt thereof,
wherein:
A is selected from aryl, heteroaryl, and heterocyclyl, each of which may be optionally substituted with 1, 2, or 3 substituents;
$R^1$ is $C_6$-$C_{20}$ alkyl;
$R^2$ is selected from hydrogen and —COOH; and
n is 1 or 2.

In some embodiments, A is phenyl, which is unsubstituted or substituted with 1, 2, 3, or 4 substituents independently selected from $C_1$-$C_4$ alkyl, $C_1$-$C_4$ alkoxy, and halo. In some embodiments, A is phenyl that is substituted with 1, 2, 3, or 4 substituents independently selected from methyl, methoxy, and isopropoxy. In some embodiments, A is phenyl substituted with 1 substituent selected from methoxy and isopropoxy. In some embodiments, A is phenyl substituted with 2 substituents independently selected from methyl and methoxy. In some embodiments, A is phenyl substituted with 3 substituents independently selected from methyl and methoxy. In some embodiments, A is phenyl substituted with 4 substituents independently selected from methyl and methoxy.

In some embodiments, A is a 5- or 6-membered monocyclic heteroaryl that is unsubstituted or substituted with 1, 2, or 3 substituents independently selected from $C_1$-$C_4$ alkyl, $C_1$-$C_4$ alkoxy, and halo. In some embodiments, A is a 5-membered monocyclic heteroaryl having 1, 2, or 3 heteroatoms independently selected from O, N, and S, and which is unsubstituted or substituted with 1, 2, or 3 substituents independently selected from $C_1$-$C_4$ alkyl, $C_1$-$C_4$ alkoxy, and halo. In some embodiments, A is a 5-membered monocyclic heteroaryl having one heteroatom selected from O, N, and S, and which is unsubstituted or substituted with 1 or 2 substituents independently selected from $C_1$-$C_4$ alkyl, $C_1$-$C_4$ alkoxy, and halo. In some embodiments, A is furanyl that is substituted with 1 substituent selected from halo (e.g., chloro or bromo).

In some embodiments, A is a bicyclic heterocyclyl group that is unsubstituted or substituted with 1, 2, or 3 substituents independently selected from $C_1$-$C_4$ alkyl, $C_1$-$C_4$ alkoxy, and halo. In some embodiments, A is a bicyclic heterocyclyl group that is unsubstituted. In some embodiments, A is selected from 2,3-dihydrobenzofuranyl and chromanyl.

In some embodiments, $R^1$ is $C_8$-$C_{14}$ alkyl. In some embodiments, $R^1$ is $C_{12}$ alkyl.

In some embodiments, $R^2$ is hydrogen. In some embodiments, $R^2$ is —COOH.

In some embodiments, n is 1. In some embodiments, n is 2.

In some embodiments, the compound is in the from of an alkali metal salt such as a sodium salt.

In some embodiments, the compound of formula (I) is selected from:
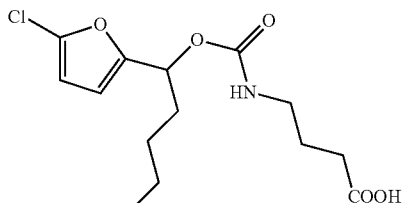
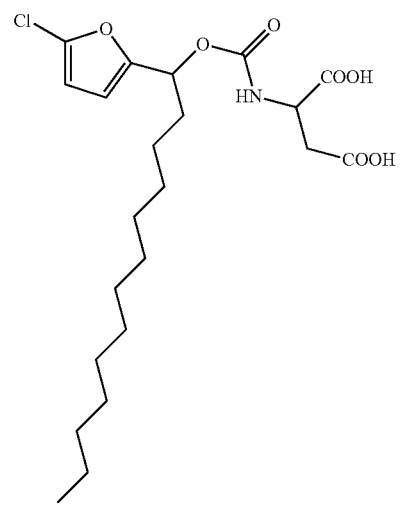
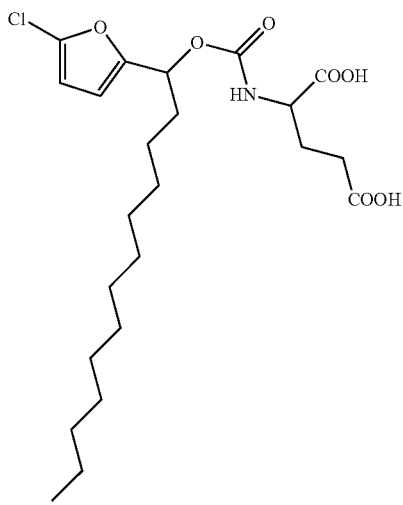
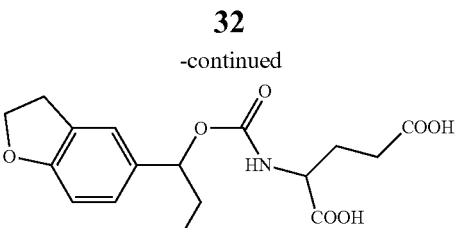
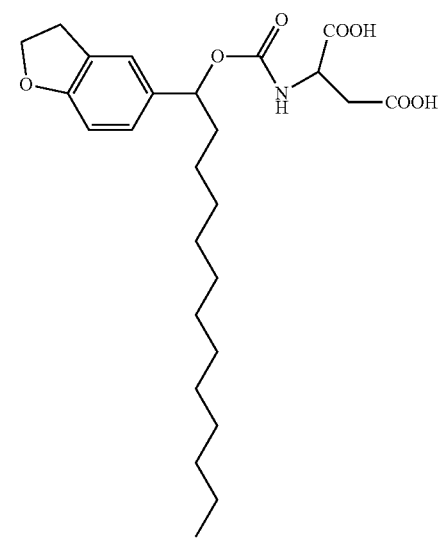
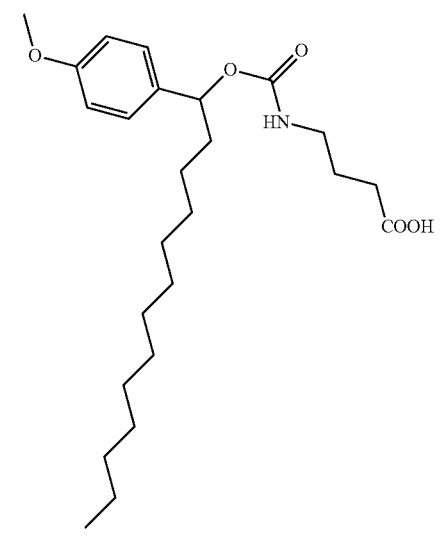

-continued

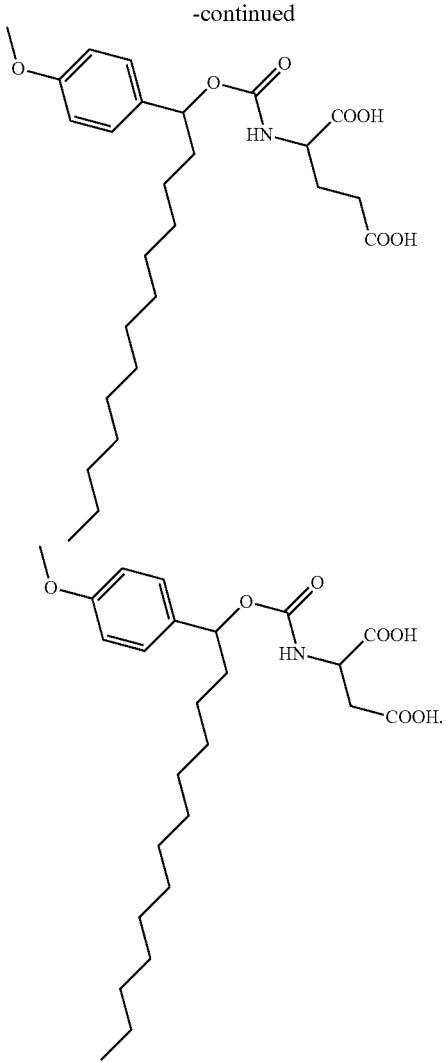

and

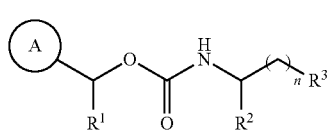

In another aspect, the disclosure provides compositions and methods, such as those further described herein, that use a compound of formula (II):

$$\text{(II)}$$

or a salt thereof,
wherein:
A is selected from a monocyclic or bicyclic aryl, heteroaryl, or heterocyclyl group, each of which may be optionally substituted with 1, 2, or 3 substituents;
$R^1$ is $C_6$-$C_{10}$ alkyl;
$R^2$ is selected from hydrogen and —COOH;
n is 1 or 2; and
$R^3$ is selected from —COOH and —$SO_3$X,
wherein X is selected from hydrogen, an alkali metal cation, or an ammonium cation.

In some embodiments, A is phenyl, which is unsubstituted or substituted with 1, 2, 3, or 4 substituents independently selected from $C_1$-$C_4$ alkyl, $C_1$-$C_4$ alkoxy, and halo. In some embodiments, A is phenyl that is substituted with 1, 2, 3, or 4 substituents independently selected from methyl, methoxy, and isopropoxy. In some embodiments, A is phenyl substituted with 1 substituent selected from methoxy and isopropoxy. In some embodiments, A is phenyl substituted with 2 substituents independently selected from methyl and methoxy. In some embodiments, A is phenyl substituted with 3 substituents independently selected from methyl and methoxy. In some embodiments, A is phenyl substituted with 3 substituents independently selected from methyl and methoxy.

In some embodiments, A is a 5- or 6-membered monocyclic heteroaryl that is unsubstituted or substituted with 1, 2, or 3 substituents independently selected from $C_1$-$C_4$ alkyl, $C_1$-$C_4$ alkoxy, and halo. In some embodiments, A is a 5-membered monocyclic heteroaryl having 1, 2, or 3 heteroatoms independently selected from O, N, and S, and which is unsubstituted or substituted with 1, 2, or 3 substituents independently selected from $C_1$-$C_4$ alkyl, $C_1$-$C_4$ alkoxy, and halo. In some embodiments, A is a 5-membered monocyclic heteroaryl having one heteroatom selected from O, N, and S, and which is unsubstituted or substituted with 1 or 2 substituents independently selected from $C_1$-$C_4$ alkyl, $C_1$-$C_4$ alkoxy, and halo. In some embodiments, A is furanyl that is substituted with 1 substituent selected from halo (e.g., chloro or bromo).

In some embodiments, A is a bicyclic heterocyclyl group that is unsubstituted or substituted with 1, 2, or 3 substituents independently selected from $C_1$-$C_4$ alkyl, $C_1$-$C_4$ alkoxy, and halo. In some embodiments, A is a bicyclic heterocyclyl group that is unsubstituted. In some embodiments, A is selected from 2,3-dihydrobenzofuranyl and chromanyl.

In some embodiments, $R^1$ is $C_8$-$C_{14}$ alkyl. In some embodiments, $R^1$ is $C_{12}$ alkyl.

In some embodiments, $R^2$ is hydrogen. In some embodiments, $R^2$ is —COOH.

In some embodiments, n is 1. In some embodiments, n is 2.

In some embodiments, $R^3$ is —COOH. In some embodiments, $R^3$ is —$SO_3$X, wherein X is a sodium cation.

In some embodiments, n is 2 and $R^3$ is —$SO_3$X, wherein X is Na.

In some embodiments, $R^1$ is $C_{12}$ alkyl, $R^2$ is hydrogen, n is 2, and $R^3$ is —$SO_3$X, wherein X is Na.

In some embodiments, the compound of formula (II) is selected from:

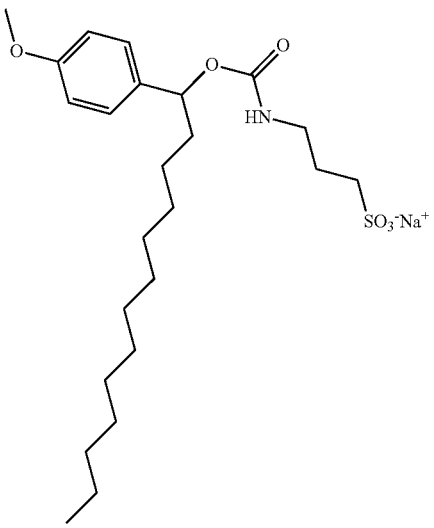

35
-continued
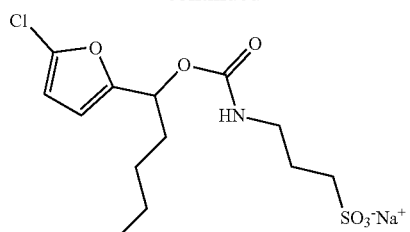
36
-continued
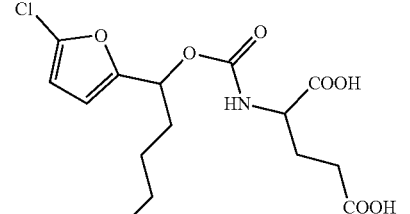
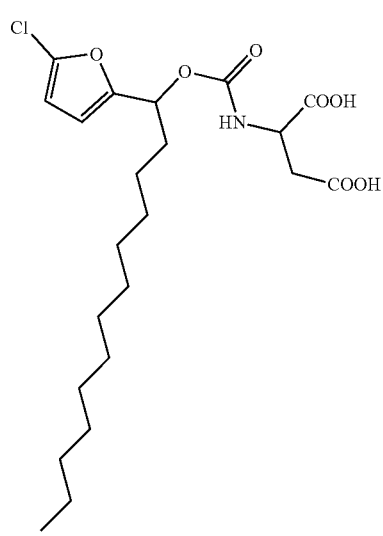
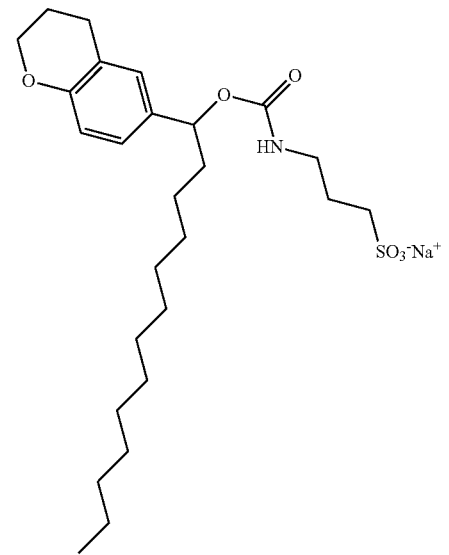

37
-continued
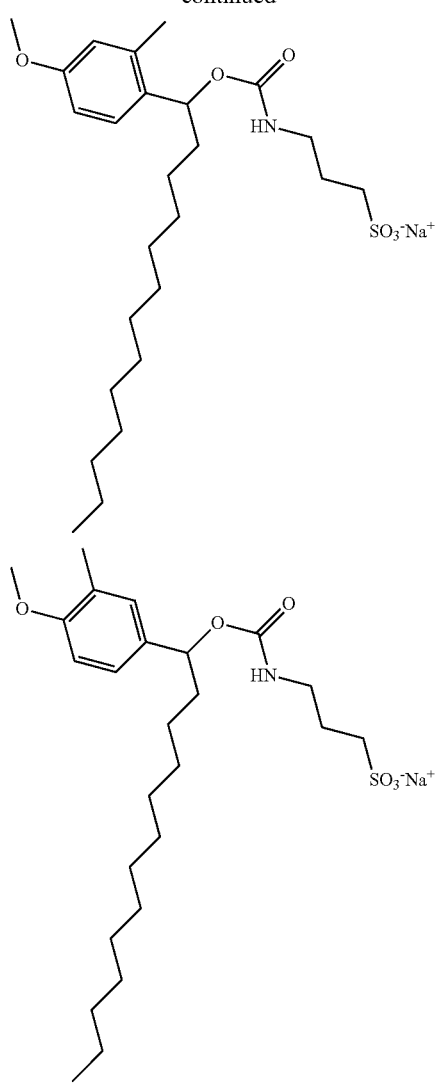
38
-continued
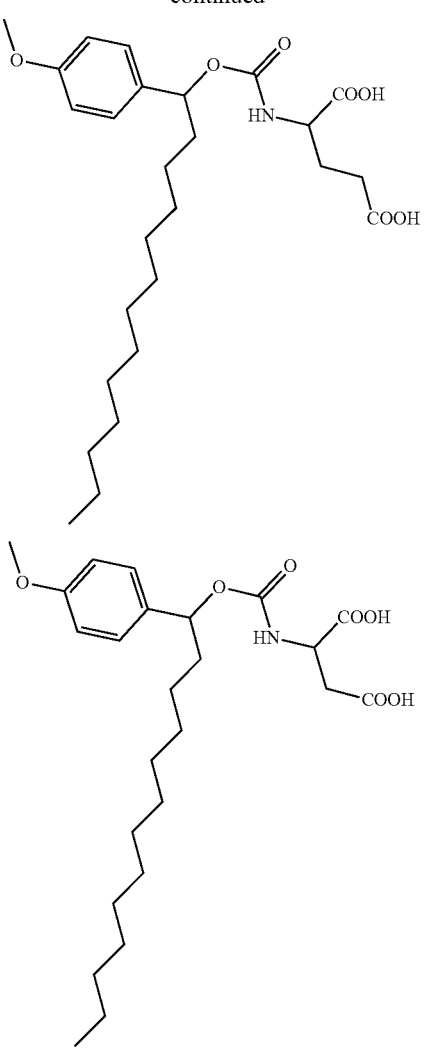
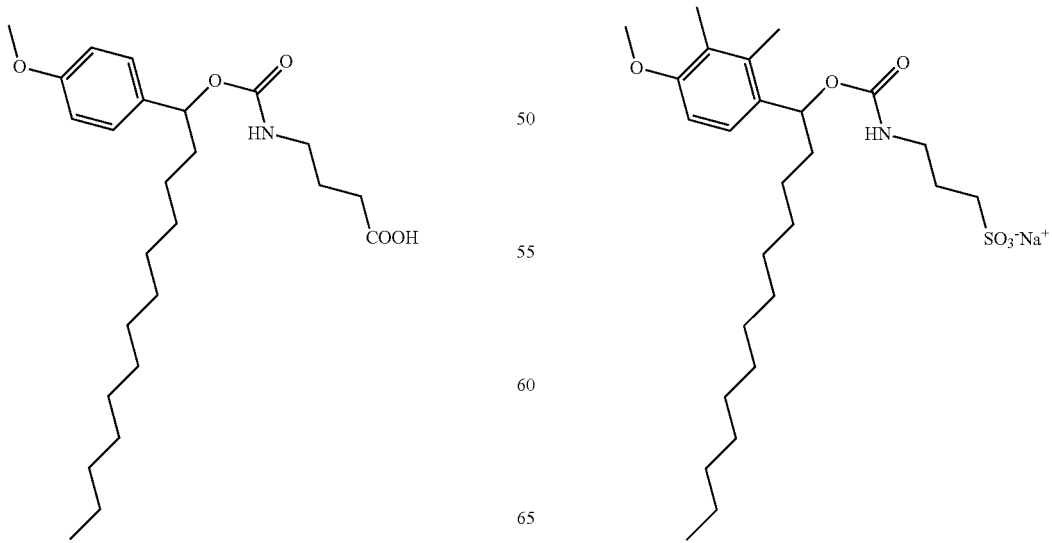

39
-continued
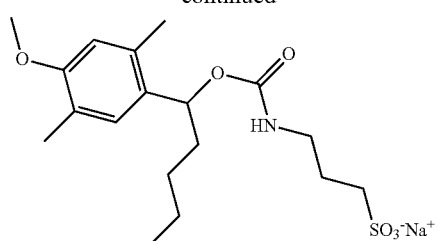
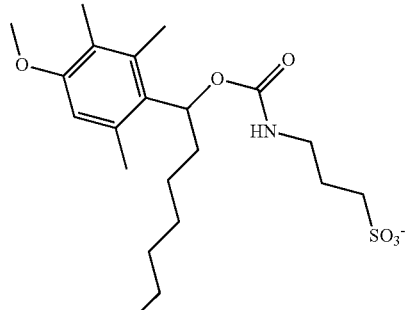
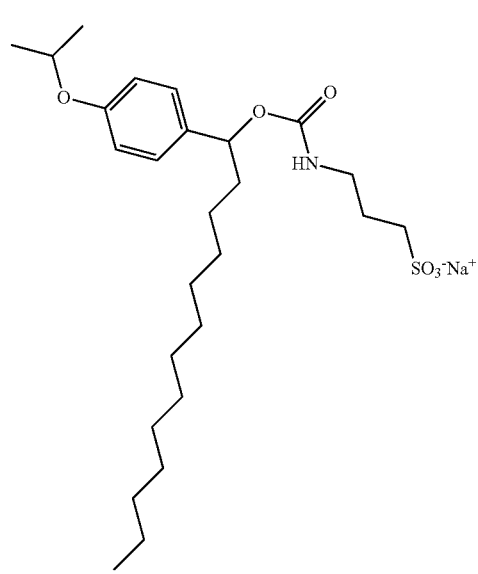
40
-continued
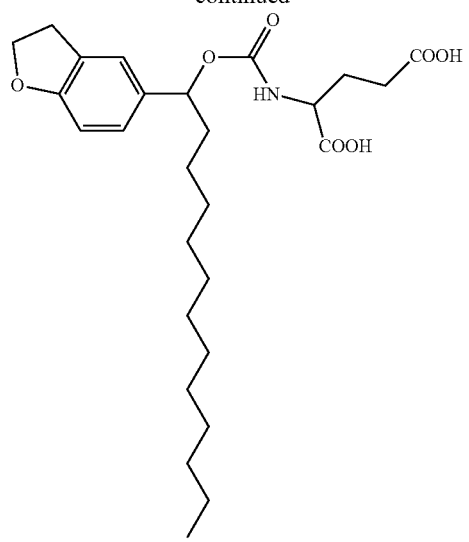
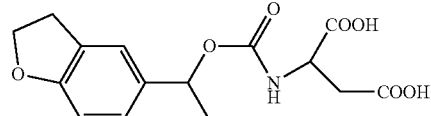
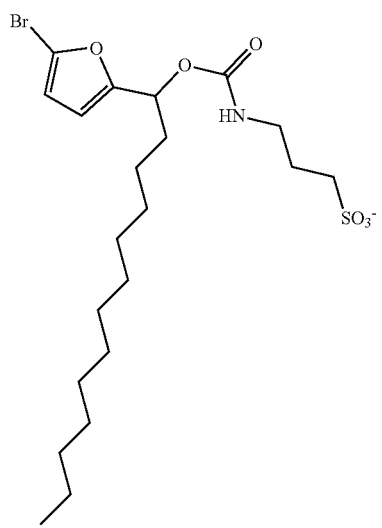

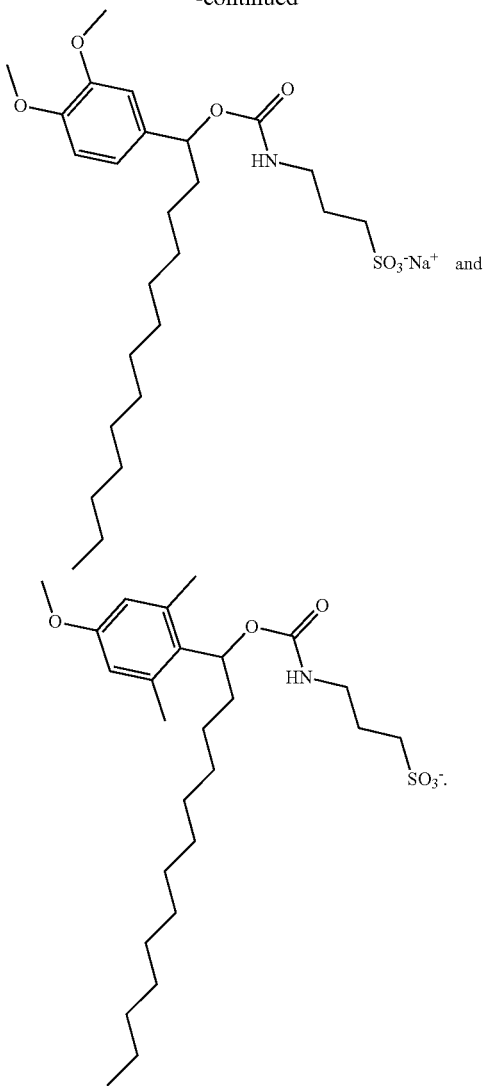

Compounds of formula (I) and formula (II) can be in the form of a salt. A neutral form of the compound may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

In particular, compounds of formula (I) include at least one —COOH moiety that may be anionic (i.e. —COO$^-$) and form a salt with a suitable cation. Compounds of formula (II) include at least one —COOH moiety or at least one —SO$_3$H moiety that may be anionic (i.e. —COO$^-$ or —SO$_3^-$ respectively) and form a salt with a suitable cation. Examples of suitable inorganic cations include, but are not limited to, alkali metal cations such as Li$^+$, Na$^+$, and K$^+$, alkaline earth cations such as Ca$^{2+}$ and Mg$^{2+}$, and other cations. Sodium salts may be particularly suitable. Examples of suitable organic cations include, but are not limited to, ammonium ion (i.e., NH$_4^+$) and substituted ammonium ions (e.g., NH$_3$R$_1^+$, NH$_2$R$_2^+$, NHR$_3^+$, NR$_4^+$. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids such as lysine and arginine.

If the compound is cationic or has a functional group that may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric.

Compounds of formula (I) and (II) can be prepared by a variety of methods. For example, compounds can be prepared as illustrated in Scheme 1.

Scheme 1

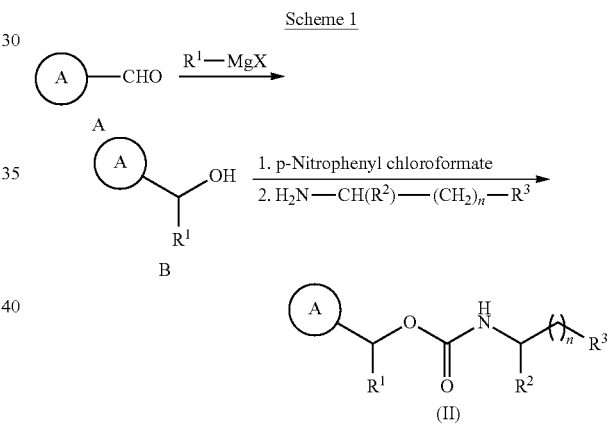

As illustrated in scheme 1, an aldehyde compound A can be reacted with a suitable Grignard reagent (e.g., a compound R$^1$—MgX where X is a halogen such as bromo) to generate compound B. Reaction of compound B with p-nitrophenyl chloroformate to generate the corresponding carbonate compound, which can be reacted with an appropriate amine to form the compound of formula (II). One skilled in the art will recognize that compounds of formula (I) can be prepared similarly using compounds in which R$^3$ is —COOH.

The compounds and intermediates herein may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

Reaction conditions and reaction times for each individual step can vary depending on the particular reactants employed and substituents present in the reactants used. Specific procedures are provided in the Examples section. Reactions can be worked up in the conventional manner, e.g., by eliminating the solvent from the residue and further purified according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups, and the methods for protecting and deprotecting different substituents using such suitable protecting groups, are well known to those skilled in the art; examples of which can be found in the treatise by PGM Wuts entitled "Greene's Protective Groups in Organic Synthesis" (5th ed.), John Wiley & Sons, Inc. (2014), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step) or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material or by resolution of a mixture of the geometric isomers of the compound or intermediates using a standard procedure such as chromatographic separation.

The synthetic schemes and specific examples as described are illustrative and are not to be read as limiting the scope of the invention as it is defined in the claims. All alternatives, modifications, and equivalents of the synthetic methods and specific examples are included within the scope of the claims.

3. PCR REAGENTS, COMPOSITIONS, AND KITS

Embodiments of the present disclosure include various reagents used to carry out PCR reactions, including, but not limited to, hot-start PCR reactions. Such PCR reactions may be performed with any suitable reagents, as described herein, including the novel thermally-labile small molecule DNA polymerase inhibitors of the present disclosure. DNA polymerases that can be used in accordance with these embodiments include, but are not limited to, any polymerase capable of replicating a DNA molecule. In some embodiments, DNA polymerases are thermostable polymerases, which are especially useful in PCR applications. Thermostable polymerases are isolated from a wide variety of thermophilic bacteria, such as *Thermus aquaticus* (Taq), *Thermus brockianus* (Tbr), *Thermus flavus* (Tfl), *Thermus ruber* (Tru), *Thermus thermophilus* (Tth), *Thermococcus litoralis* (Tli) and other species of the *Thermococcus* genus, *Thermoplasma acidophilum* (Tac), *Thermotoga neapolitana* (Tne), *Thermotoga maritima* (Tma), and other species of the *Thermotoga* genus, *Pyrococcus furiosus* (Pfu), *Pyrococcus woesei* (Pwo) and other species of the *Pyrococcus genus*, *Bacillus sterothermophilus* (Bst), *Sulfolobus acidocaldarius* (Sac) *Sulfolobus solfataricus* (Sso), *Pyrodictium occultum* (Poc), *Pyrodictium abyssi* (Pab), and *Methanobacterium thermoautotrophicum* (Mth), and mutants, variants or derivatives thereof.

In some embodiments, DNA polymerases that can be used in accordance with these embodiments include, but are not limited to, commercially available DNA polymerases (e.g., from Boehringer Mannheim Corp., Indianapolis, Ind.; Life Technologies, Inc., Rockville, Md.; New England Biolabs, Inc., Beverley, Mass.; Perkin Elmer Corp., Norwalk, Conn.; Pharmacia LKB Biotechnology, Inc., Piscataway, N.J.; Qiagen, Inc., Valencia, Calif.; Stratagene, La Jolla, Calif). In some embodiments, a DNA polymerase is Taq, Tbr, Tfl, Tru, Tth, Tli, Tac, Tne, Tma, Tih, Tfi, Pfu, Pwo, KOD, Bst, Sac, Sso, Poc, Pab, Mth, Pho, ES4, VENT®, DEEPVENT®, and active mutants, variants and derivatives thereof. Other DNA polymerases can be used in conjunction with the novel thermal labile small molecule DNA polymerase inhibitors provided herein, including DNA polymerases not specifically disclosed above, but would be known to one of ordinary skill in the art based on the present disclosure.

In accordance with the embodiments provided herein, various other PCR reagents can include an amplification reagent, which may include at least one primer or at least one pair of primers for amplification of a nucleic acid target, at least one probe and/or dye to enable detection of amplification, a ligase, a detergent (e.g., non-ionic detergents), nucleotides (dNTPs and/or NTPs), divalent magnesium ions, or any combination thereof, among others that would be recognized by one of ordinary skill in the art based on the present disclosure. In some embodiments, an amplification reagent and/or a nucleic acid target each may be present at an effective amount, such as an amount sufficient to enable amplification of a desired nucleic acid target in the presence of other necessary reagents, including, but not limited to, a thermostable reverse transcriptase and manganese.

In accordance with the embodiments provided herein, PCR reagents can include one or more primers, or any nucleic acid capable of, and/or used for, priming replication of a nucleic acid template. Generally, a primer is a shorter nucleic acid that is complementary to a longer template. During replication, the primer may be extended, based on the template sequence, to produce a longer nucleic acid that is a complementary copy of the template. Extension may occur by successive addition of individual nucleotides (e.g., by the action of a polymerase) or by attachment of a block of nucleotides (e.g., by the action of a ligase joining a pair of primers), among others. A primer may be DNA, RNA, an analog thereof (e.g., an artificial nucleic acid), or any combination thereof. A primer may have any suitable length, such as at least about 10, 15, 20, or 30 nucleotides. Exemplary primers are synthesized chemically. Primers may be supplied as at least one pair of primers for amplification of at least one nucleic acid target. A pair of primers may be a sense primer and an antisense primer that collectively define the opposing ends (and thus the length) of a resulting amplicon.

In accordance with the embodiments provided herein, PCR reagents can also include one or more probes, or any nucleic acid connected to at least one label, such as at least one dye. A probe may be a sequence-specific binding partner for a nucleic acid target and/or amplicon. The probe may be designed to enable detection of target amplification based on fluorescence resonance energy transfer (FRET), including one or more nucleic acids connected to a pair of dyes that collectively exhibit fluorescence resonance energy transfer (FRET) when proximate one another. The pair of dyes may provide first and second emitters, or an emitter and a quencher, among others. Fluorescence emission from the pair of dyes changes when the dyes are separated from one another, such as by cleavage of the probe during primer extension (e.g., a 5' nuclease assay, such as with a TAQMAN probe), or when the probe hybridizes to an amplicon (e.g., a molecular beacon probe). The nucleic acid portion of the probe may have any suitable structure or origin, for example, the portion may be a locked nucleic acid, a member of a universal probe library, or the like. In other cases, a probe and one of the primers of a primer pair may be combined in the same molecule. For example, the primer-probe molecule may include a primer sequence at its 3' end and a molecular beacon-style probe at its 5' end. With this arrangement, related primer-probe molecules labeled with different dyes can be used in a multiplexed assay with the same reverse primer to quantify target sequences differing by a single nucleotide (single nucleotide polymorphisms (SNPs)).

In some embodiments, PCR reagents can also include one or more labels or reporter molecules. A label includes any identifying and/or distinguishing marker or identifier connected to or incorporated into any entity such as a compound, biological particle (e.g., a DNA, a RNA, a cell, bacteria, spore, virus, or organelle), or droplet. A label may, for example, be a dye that renders an entity optically detectable and/or optically distinguishable. Exemplary dyes used for labeling are fluorescent dyes (fluorophores) and fluorescence quenchers. A reporter includes any compound or set of compounds that reports a condition such as the extent of a reaction. Exemplary reporters comprise at least one dye, such as a fluorescent dye or an energy transfer pair, and/or at least one oligonucleotide. Exemplary reporters for nucleic acid amplification assays may include a probe and/or an intercalating dye (e.g., SYBR Green, ethidium bromide, etc.).

In some embodiments, one or more PCR reagents can be combined to form a composition or a kit. In some embodiments, a composition can include any suitable PCR reagents that are required for carrying out an amplification reaction including the novel thermally-labile small molecule DNA polymerase inhibitors of the present disclosure. For example, compositions can include a DNA polymerase inhibitor of the present disclosure and one or more PCR reagents such as one or more of a primer or pair of primers for amplification of a nucleic acid target, a probe and/or dye to enable detection of amplification, a ligase, a polymerase, nucleotides (dNTPs and/or NTPs), divalent magnesium ions, or any combination thereof, among other reagents that would be recognized by one of ordinary skill in the art based on the present disclosure. These various combinations of PCR reagents, including the novel thermally-labile small molecule DNA polymerase inhibitors, can also be included in a kit used to carry out PCR reactions including hot-start PCR reactions.

In accordance with the embodiments provided herein, concentrations of the PCR reagents described above can vary, depending on specific reaction conditions and reagents used, as well as the desired DNA target to be amplified. One of skill in the art would readily recognize that any specific concentrations or concentration ranges provided herein for any PCR reagents, including concentration ranges pertaining to the DNA polymerase inhibitors of the present disclosure, will vary depending on the specific reaction conditions and reagents used and are not meant to be limiting.

4. MATERIALS AND METHODS

Embodiments of the present disclosure include various compositions and methods used to carry out PCR reactions, including, but not limited to, hot-start PCR reactions. Generally, PCR reactions involve a process replication or forming a copy (e.g., a direct copy and/or a complementary copy) of a nucleic acid or a segment thereof. Replication reactions generally involves an enzyme, such as a polymerase and/or a ligase, among others. The nucleic acid and/or segment replicated is a template (and/or a target) for replication. PCR reactions also generally involve a process of amplification, or a reaction in which replication occurs repeatedly over time to form multiple copies of at least one segment of a template molecule. Amplification may generate an exponential or linear increase in the number of copies as amplification proceeds. Typical amplifications produce a greater than 1,000-fold increase in copy number and/or signal. Exemplary amplification reactions for the assays disclosed herein may include the polymerase chain reaction (PCR) or ligase chain reaction (LCR), each of which is driven by thermal cycling. Thermal cycling generally involves cycles of heating and cooling a reaction mixture to perform successive rounds of denaturation (melting), annealing, and extension. Additionally or alternatively, assays provided herein may use other amplification reactions, which may be performed isothermally, such as branched-probe DNA assays, cascade-RCA, helicase-dependent amplification, loop-mediated isothermal amplification (LAMP), nucleic acid based amplification (NASBA), nicking enzyme amplification reaction (NEAR), PAN-AC, Q-beta replicase amplification, rolling circle replication (RCA), self-sustaining sequence replication, strand-displacement amplification, and the like. Amplification may utilize a linear or circular template.

Amplification may be performed with any suitable reagents, as described above, including the novel thermally-labile small molecule DNA polymerase inhibitors of the present disclosure. Amplification may be performed, or tested for its occurrence, in an amplification mixture, which is any composition capable of generating multiple copies of a nucleic acid target molecule, if present, in the composition. An amplification mixture may include any combination of at least one primer or primer pair, at least one probe, at least one replication enzyme (e.g., at least one polymerase, such as at least one DNA and/or RNA polymerase, and/or at least one ligase), and/or deoxynucleotide (and/or nucleotide) triphosphates (dNTPs and/or NTPs), among others.

As described further herein, hot-start PCR amplification generally includes amplification reactions (e.g., polymerization and/or ligation) that do not amplify a specific target without also, for example, amplifying non-specific targets, until an elevated temperature is reached. The elevated temperature may be at least about the annealing temperature for the primers to reduce non-specific amplification. In some cases, hot-start PCR allows for the amplification of a given target, or the amplification of an increased yield of a given target and is not necessarily required to reduce amplification of non-specific targets. In other cases, the nuclease activity of a polymerase enzyme can cause degradation of primers and templates (e.g., resulting in the removal of fluorescent dyes, or decrease in primer or probe length); and, in some cases, hot-start PCR can reduce or prevent undesired nuclease activity.

Generally, PCR includes any nucleic acid amplification reaction that relies on alternating cycles of heating and cooling (i.e., thermal cycling) to achieve successive rounds of replication. PCR may be performed by thermal cycling between two or more temperature set points, such as a higher melting (denaturation) temperature and a lower annealing/extension temperature, or among three or more temperature set points, such as a higher melting temperature, a lower annealing temperature, and an intermediate extension temperature, among others. PCR may be performed with a heat-stable polymerase, such as Taq DNA polymerase (e.g., wild-type enzyme, a Stoffel fragment, FastStart polymerase, etc.), Pfu DNA polymerase, S-Tbr polymerase, Tth polymerase, Vent polymerase, or a combination thereof, among others described above. PCR generally produces an exponential increase in the amount of a product amplicon over successive cycles.

Any suitable PCR methodology or combination of methodologies may be utilized in the embodiments disclosed herein, such as allele-specific PCR, assembly PCR, asymmetric PCR, digital PCR, endpoint PCR, hot-start PCR, in situ PCR, intersequence-specific PCR, inverse PCR, linear after exponential PCR, ligation-mediated PCR, methylation-specific PCR, miniprimer PCR, multiplex ligation-dependent probe amplification, multiplex PCR, nested PCR, overlap-extension PCR, polymerase cycling assembly, qualitative PCR, quantitative PCR, real-time PCR, RT-PCR, single-cell PCR, solid-phase PCR, thermal asymmetric interlaced PCR, touchdown PCR, universal fast walking PCR, or any combination thereof, among others.

In accordance with embodiments described above, various materials and methods used to investigate the thermal labile small molecule polymerase inhibitors of the present disclosure are described below.

Figure 9:
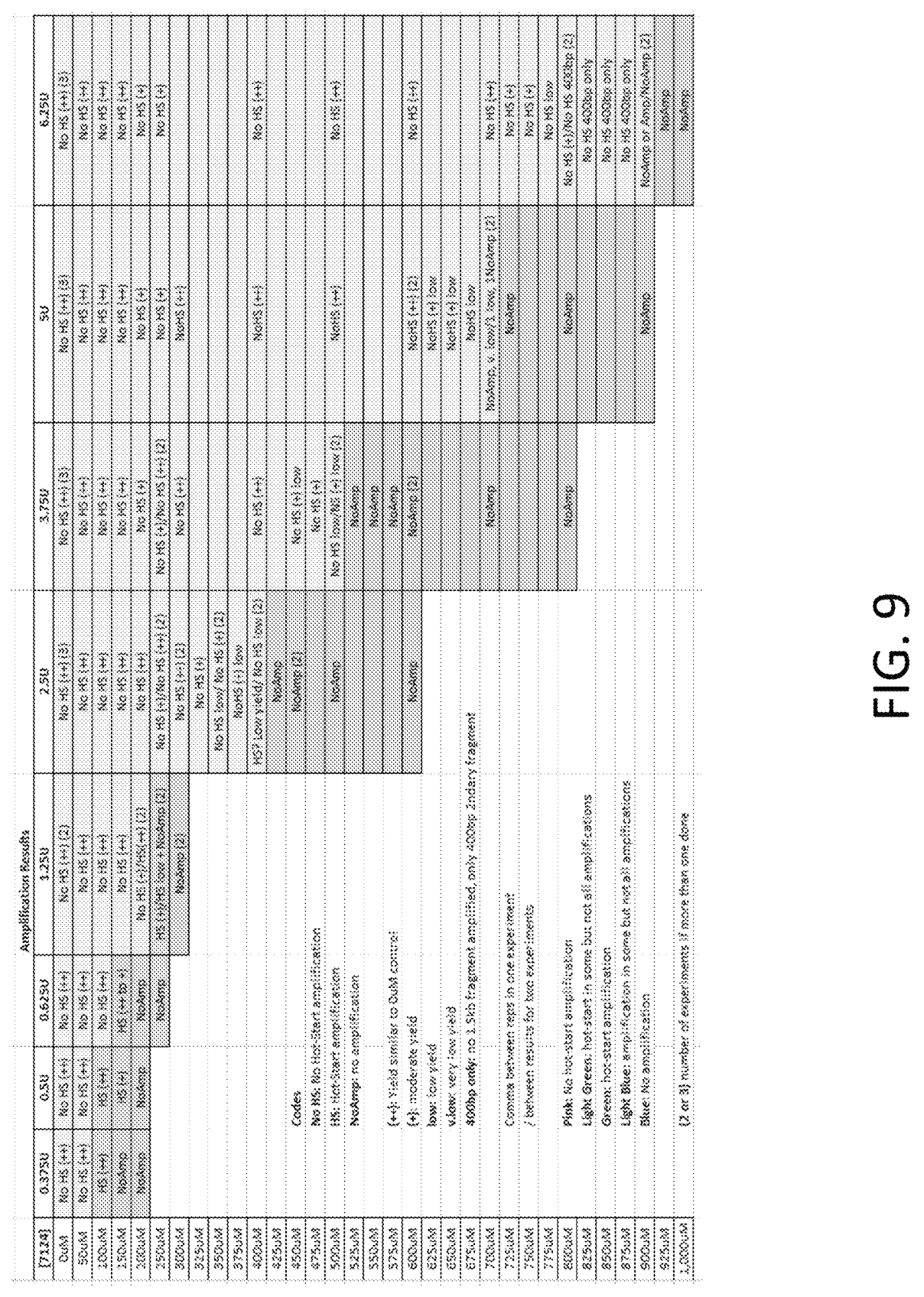

Taq and Thermal Degradable Detergent Titrations. FIG. 9 includes a representative table of the results of various hot-start PCR reactions (Corynephage omega gene target) performed with polymerase inhibitor compound #7124 and polymerase enzyme at the various concentrations shown. Ranges included from about 0.375 to 1.25 U Taq/25 µl reaction and from 100-250 µM of compound #7124. FIG. 10 includes a representative table of the results of various hot-start PCR reactions performed with polymerase inhibitor compound #7261 and polymerase enzyme at the various concentrations shown. Ranges included from about 0.375 to 1.25 U Taq/25 µl reaction, and from 50-175 µM of compound #7216. (See Table 1 below.)

TABLE 1

| Taq Level in Figure | U Taq/25 ul reaction | U Taq/ul reaction |
| --- | --- | --- |
| 0.375 U | 0.375 U/25 ul reaction | 0.0056 U/ul |
| 0.5 U | 0.5 U/25 ul reaction | 0.01 U/ul |
| 0.625 U | 0.625 U/25 ul reaction | 0.025 U/ul |
| 1.25 U | 1.25 U/25 ul reaction | 0.05 U/ul |
| 2.5 U | 2.5 U/25 ul reaction | 0.1 U/ul |
| 3.75 U | 3.75 U/25 ul reaction | 0.15 U/ul |
| 5 U | 5 U/25 ul reaction | 0.2 U/ul |
| 6.25 U | 6.25 U/25 ul reaction | 0.25 U/ul |

Figure 11:
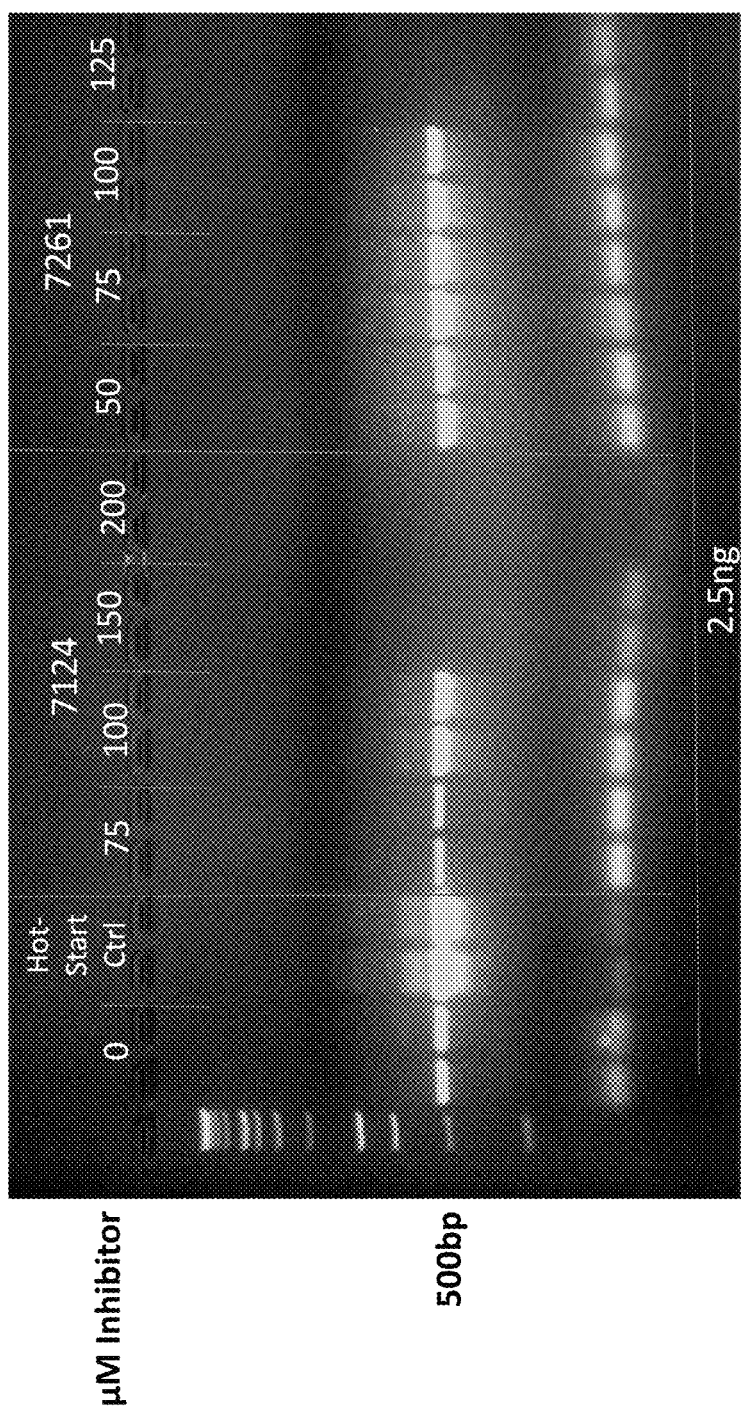
FIG. 11 includes a representative image of an agarose gel used to evaluate the CCR5 gene amplification products of various hot-start PCR reactions performed with and without two different polymerase inhibitors (compound #7124 and compound #7261) using human genomic DNA as a template.

Testing of Human Genomic Templates. FIG. 11 includes a representative image of an agarose gel used to evaluate the CCR5 gene amplification products of various hot-start PCR reactions performed with and without two different polymerase inhibitors (compound #7124 and compound #7261) and using human genomic DNA as a template. The target amplicon is 500 bp, and without the use of hot-start, there is a significant amount of primer dimer. With compound #7124 and compound #7261, the 500 bp yield increased, but primer dimer amounts remained (compare to GoTaq® DNA Polymerase treatment for no hot-start and GoTaq® Hot-Start DNA Polymerase with an antibody-mediated hot-start). Reaction components are provided in Table 2 below; the following cycling methods were used: [(22° C. for 90 min, 94° C. for 2 min) 1 cycle, (92° C. for 30 sec, 68° C. for 2 min) 45 cycles, (72° C. for 5 min) 1 cycle, 4° C. soak].

Figure 12:
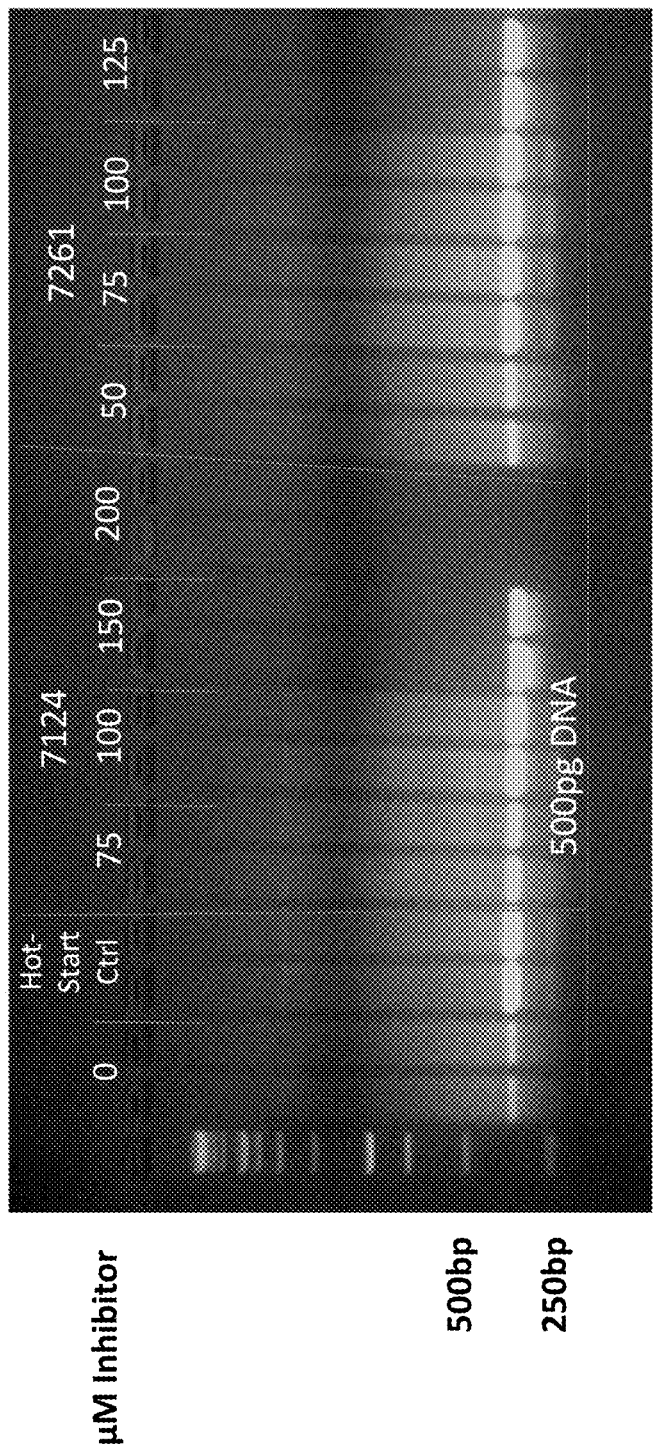
FIG. 12 includes a representative image of an agarose gel used to evaluate the Human Dystrophin Alu 7-2 gene amplification products of various hot-start PCR reactions performed with and without two different polymerase inhibitors (compound #7124 and compound #7261) using human genomic DNA as a template.

FIG. 12 includes a representative image of an agarose gel used to evaluate the Human Dystrophin Alu-72 gene amplification products of various hot-start PCR reactions performed with and without two different polymerase inhibitors (compound #7124 and compound #7261) and using human genomic DNA as a template. The target amplicon is 320 bp, and without hot-start, there is less yield. With compound #7124 and compound #7261, the 320 bp yield increased, and at certain concentrations, secondary products (seen as a smear) dramatically decreased. Reaction components are provided in Table 2 below; the following cycling methods were used: [(22° C. for 90 min, 94° C. for 2 min) 1 cycle, (94° C. for 50 sec, 59° C. for 50 sec, 68° C. for 2 min) 42 cycles, 4° C. soak].

TABLE 2

| Component | Corynephage omega gene | CCR5 Hot-Start | HD Alu 7-2 Hot-Start |
| --- | --- | --- | --- |
| Small Molecule Inhibitor | | | |
| Taq | 0.025 U/ul reaction | 0.025 U/ul reaction | 0.025U/ul reaction |
| Primers | 0.4 uM | 0.4 uM | 0.2 uM |
| Detergent: PPD (Promega Proprietary Detergent) | 0.0025%, variable when did Taq titration expts FIG. 9 & 10 | 0.0025% | 0.0025% |

TABLE 2-continued

| Component | Corynephage omega gene | CCR5 Hot-Start | HD Alu 7-2 Hot-Start |
|---|---|---|---|
| Detergent: PPD (Promega Proprietary Detergent) | 0.0025%, variable when did Taq titration expts FIG. 9 & 10 | 0.0025% | 0.0025% |
| dNTPs (each) | 0.2 mM | 0.2 mM | 0.2 mM |
| Mg | 2 mM | 2 mM | 2 mM |
| Template: plasmid | 0.5 ng/25 ul Rxn | NA | NA |
| Template: Human Genomic | NA | 100 pg/ul (2.5 ng), 10 pg/ul (250 pg), 1 pg/ul (25 pg) | 10 pg/ul (500 pg), 1 pg/ul (50 pg), 0.1 pg/ul (5 pg) |

5. EXAMPLES

It will be readily apparent to those skilled in the art that other suitable modifications and adaptations of the methods of the present disclosure described herein are readily applicable and appreciable and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Compound Syntheses

Polymerase inhibitors can be made by the following general procedures.

Aldehyde (1 equivalent) reacted with the desired Grignard reagent (1.2 equivalent) in dry THF at 0° C. The mixture was stirred at RT overnight. The reaction was quenched by adding 20 mL of water and then 100 mL of ether added. The resulting mixture was acidified by 2N HCl until the precipitates disappeared. The aqueous layer was extracted three times with ether, and the combined organic layer was washed with water and dried over $Na_2SO_4$. The resulting alcohol was purified by silica column using heptane/ethyl acetate as the eluent.

To the solution of the above alcohol (1 equivalent) and p-nitrophenylchloroformate (2 equivalent) in 20 mL dry THF, pyridine (3 equivalent) was added slowly at 0° C. The reaction mixture was stirred for 1 hour. After removing the solvent, the residue was dissolved in heptane. The insoluble precipitate was filtered out. After removing the solvent of filtrate, the crude p-nitrophenylcarbonate was used directly.

To the solution of p-nitrophenylcarbonate (1 equivalent), the desired amine TBA salt (3 equivalent) was added. The mixture was stirred for 1 hour. The solid was removed by filtration. After removal of the solvent, the compound was dissolved in DCM and purified by silica column using heptane/ethyl acetate to DCM/MeOH as solvent. The viscous solid was obtained. Bisodium resin was washed with deionized water 3-4 times. The compound was loaded to resin column for ion-exchange. The compound was rinsed out quickly, and the desired fractions were collected and lyophilized.

Compound structures are listed below.

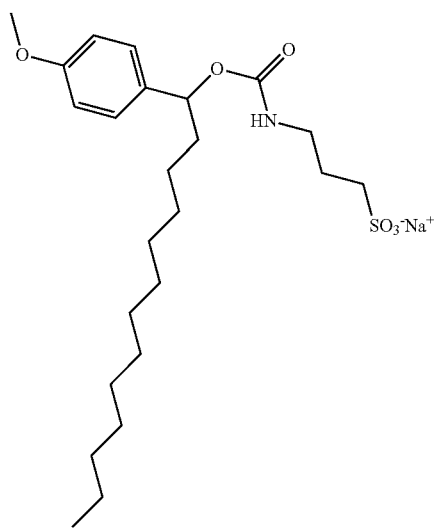

7124

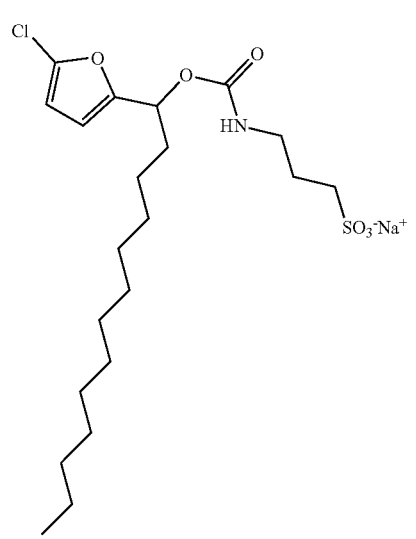

7261

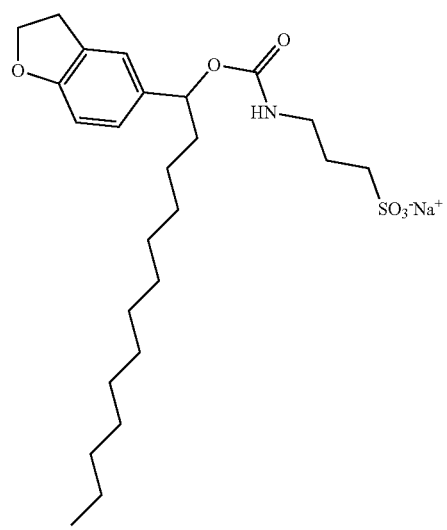
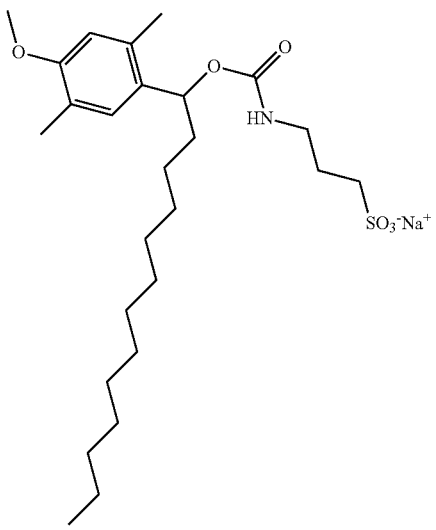
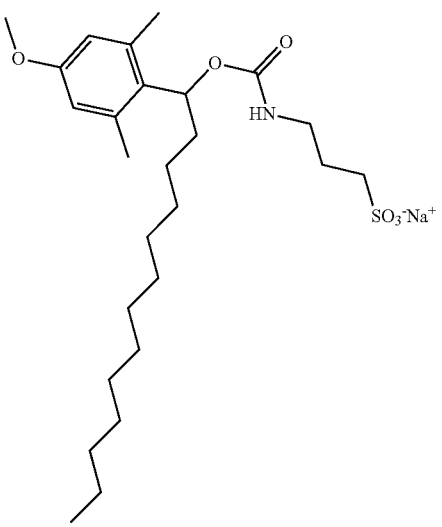
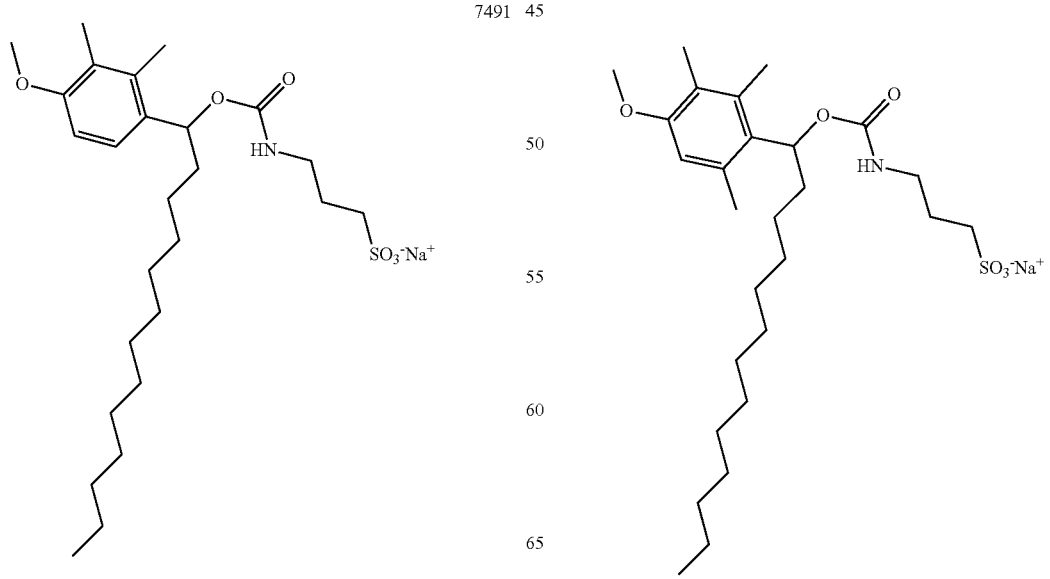

7484
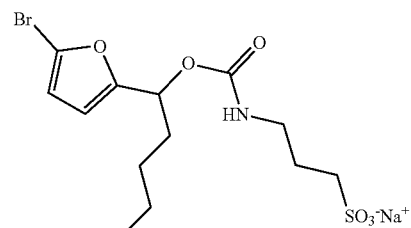
7487
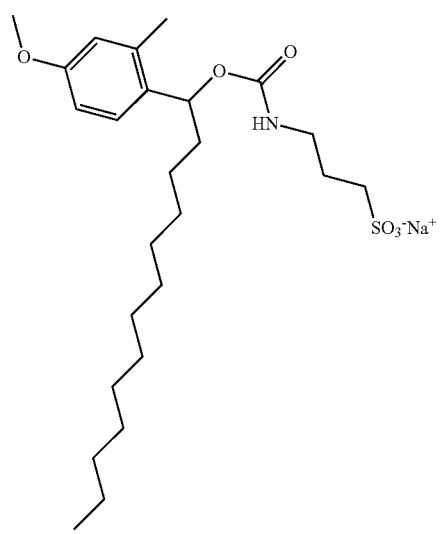
7488
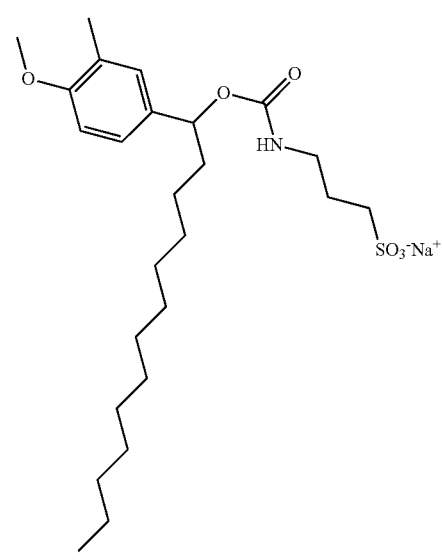
7486
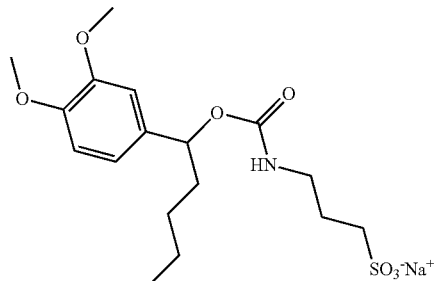
7495
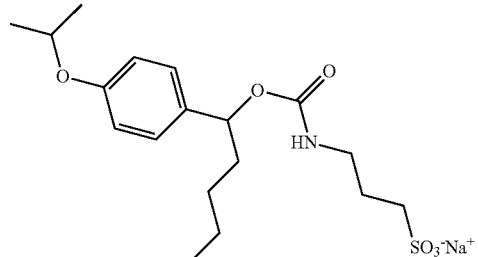
7365
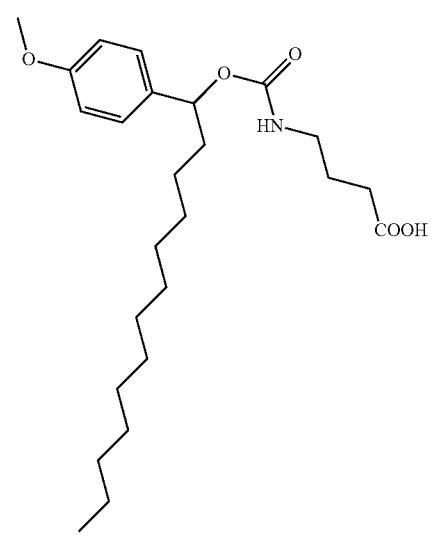

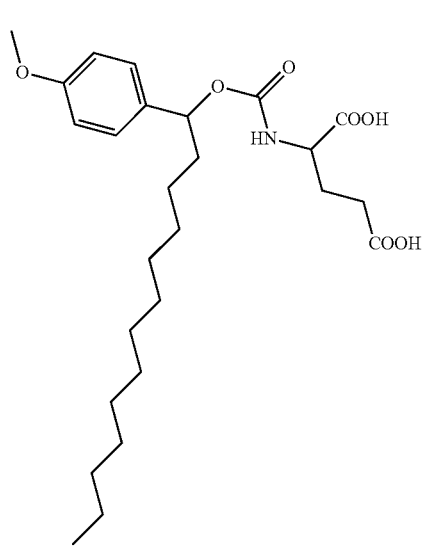
7366
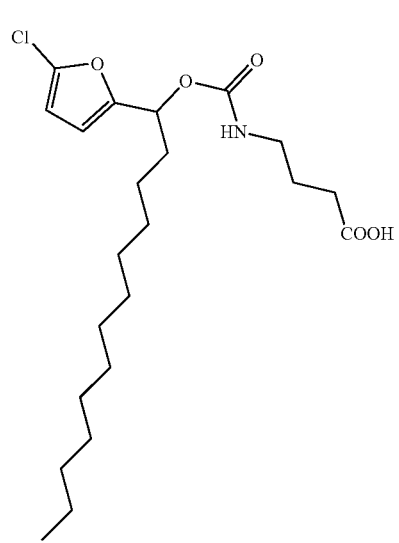
7437
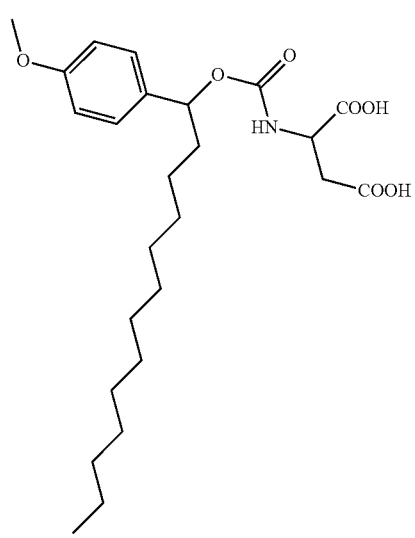
7367
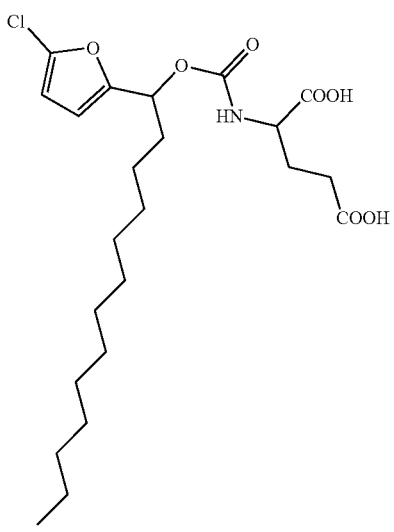
7439
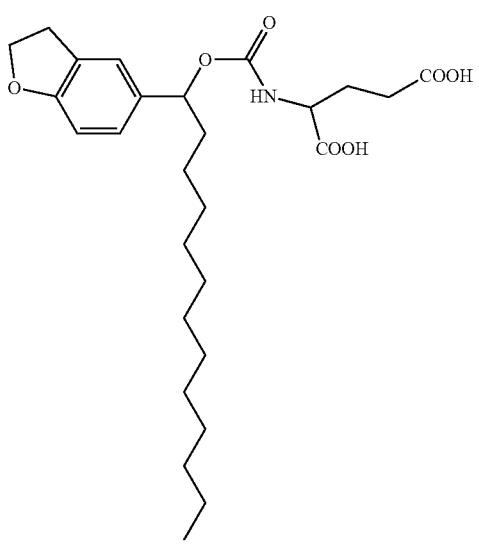
7630
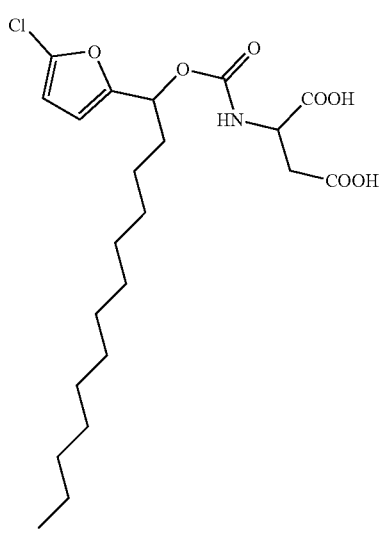
7438

-continued

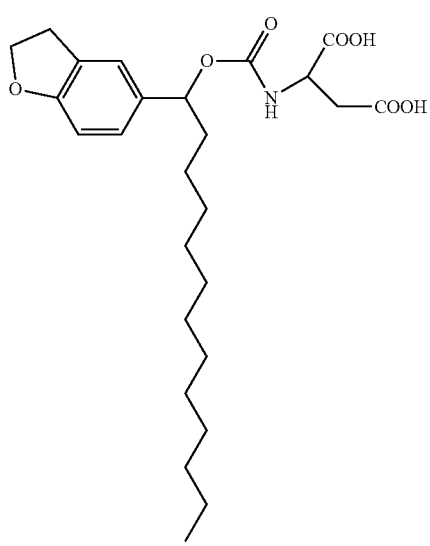

7629

Sodium 3-((((1-(4-methoxyphenyl)tridecyl)oxy)carbonyl)amino)propane-1-sulfonate (7124). $^1$H NMR (d$^6$-DMSO, δ ppm): 7.25 (d, 2H), 7.15 (t, 1H), 6.82 (d, 2H), 5.48 (t, 1H, CH), 3.73 (s, 3H, OCH3), 2.93 (m, 2H, CH2), 2.38 (t, 2H, CH2), 1.5-1.8 (m, 4H, CH2), 1.1-1.4 (m, CH2, 20H), 0.75 (t, CH3, 3H). MS (m/e) [M$^-$] (C$_{24}$H$_{40}$NO$_6$S$^-$): calculated 470.26, observed 470.3.

Sodium 3-((((1-(5-chlorofuran-2-yl)tridecyl)oxy)carbonyl)amino)propane-1-sulfonate (7261). $^1$H NMR (d$^6$-DMSO, δ ppm): 7.50 (t, 1H, NH), 6.52 (d, 1H), 6.41 (d, 1H), 5.55 (t, 1H, CH), 3.01 (q, 2H, CH2), 2.32 (t, 2H, CH2), 1.81 (q, 2H, CH2), 1.62 (m, 2H, CH2), 1.1-1.4 (m, CH2, 20H), 0.8 (t, CH3, 3H). MS (m/e) [M$^-$] (C$_{21}$H$_{35}$ClNO$_6$S): calculated 464.19, observed 464.3.

Sodium 3-((((1-(2,3-dihydrobenzofuran-5-yl)tridecyl)oxy)carbonyl)amino)propane-1-sulfonate (7489). $^1$H NMR (d$^6$-DMSO, δ ppm): 7.20 (s, 1H), 7.12 (t, 1H), 6.95 (d, 1H), 6.65 (d, 1H), 5.48 (t, 1H, CH), 4.5 (t, 2H, CH2), 3.20 (t, 2H, CH2), 2.36 (m, 2H, CH2), 2.38 (t, 2H, CH2), 1.5-1.8 (m, 4H, CH2), 1.1-1.4 (m, CH2, 20H), 0.80 (t, CH3, 3H). MS (m/e) [M$^-$](C$_{24}$H$_{40}$NO$_6$S$^-$): calculated 482.26, observed 482.5.

Sodium 3-((((1-(chroman-6-yl)tridecyl)oxy)carbonyl)amino)propane-1-sulfonate (7490). $^1$H NMR (d$^6$-DMSO, δ ppm): 7.15 (t, 1H), 6.98 (m, overlap, 2H), 6.65 (d, 1H), 5.48 (t, 1H, CH), 4.17 (t, 2H, CH2), 2.91 (m, 2H, CH2), 2.75 (t, 2H, CH2), 2.37 (t, 2H, CH2), 1.5-1.8 (m, 4H, CH2), 1.1-1.4 (m, CH2, 20H), 0.80 (t, CH3, 3H). MS (m/e) [M$^-$] (C$_{26}$H$_{42}$NO$_6$S$^-$): calculated 496.27, observed 496.6.

Sodium 3-((((1-(4-methoxy-2-methylphenyl)tridecyl)oxy)carbonyl)amino)propane-1-sulfonate (7487). $^1$H NMR (d$^6$-DMSO, δ ppm): 7.21 (d, 1H), 7.10 (t, 1H), 6.73 (d, 1H), 6.62 (s, br, 1H), 5.61 (t, 1H, CH), 3.68 (s, 3H, OCH3), 2.94 (m, 2H, CH2), 2.37 (t, 2H, CH2), 2.30 (s, 3H, CH3), (t, 2H, CH2), 1.5-1.8 (m, 4H, CH2), 1.1-1.4 (m, CH2, 20H), 0.81 (t, CH3, 3H). MS (m/e) [M$^-$](C$_{25}$H$_{42}$NO$_6$S$^-$): calculated 484.27, observed 484.5.

Sodium 3-((((1-(4-methoxy-3-methylphenyl)tridecyl)oxy)carbonyl)amino)propane-1-sulfonate (7488). $^1$H NMR (d$^6$-DMSO, δ ppm): 7.0-7.2 (m, 3H), 6.83 (d, 1H), 5.63 (t, 1H, CH), 3.63 (s, 3H, OCH3), 2.94 (m, 2H, CH2), 2.37 (t, 2H, CH2), 2.12 (s, 3H, CH3), 1.5-1.8 (m, 4H, CH2), 1.1-1.4 (m, CH2, 20H), 0.81 (t, CH3, 3H). MS (m/e) [M$^-$] (C$_{25}$H$_{42}$NO$_6$S$^-$): calculated 484.27, observed 484.5.

Sodium 3-((((1-(4-methoxy-2,3-dimethylphenyl)tridecyl)oxy)carbonyl)amino) propane-1-sulfonate (7491). $^1$H NMR (d$^6$-DMSO, δ ppm): 7.31 (t, 1H, NH), 7.11 (d, 1H), 6.73 (d, 1H), 5.67 (t, 1H, CH), 3.77 (s, 3H, OCH3), 2.91 (m, 2H, CH2), 2.37 (t, 2H, CH2), 2.19 (s, 3H, CH3), 2.12 (s, 3H, CH3), 1.5-1.8 (m, 4H, CH2), 1.1-1.4 (m, CH2, 20H), 0.81 (t, CH3, 3H). MS (m/e) [M$^-$] (C$_{26}$H$_{44}$NO$_6$S$^-$): calculated 498.29, observed 498.5.

Sodium 3-((((1-(4-methoxy-2,5-dimethylphenyl)tridecyl)oxy)carbonyl)amino) propane-1-sulfonate (7493). $^1$H NMR (d$^6$-DMSO, δ ppm): 7.13 (t, 1H, NH), 7.0 (s, 1H), 6.67 (s, 1H), 5.67 (t, 1H, CH), 3.73 (s, 3H, OCH3), 2.95 (m, 2H, CH2), 2.35 (t, 2H, CH2), 2.29 (s, 3H, CH3), 2.14 (s, 3H, CH3), 1.5-1.8 (m, 4H, CH2), 1.1-1.4 (m, CH2, 20H), 0.79 (t, CH3, 3H). MS (m/e) [M$^-$] (C$_{26}$H$_{44}$NO$_6$S$^-$): calculated 498.29, observed 498.5.

Sodium 3-((((1-(4-methoxy-2,6-dimethylphenyl)tridecyl)oxy)carbonyl)amino) propane-1-sulfonate (7494). $^1$H NMR (d$^6$-DMSO, δ ppm): 7.13 (t, 1H, NH), 6.51 (s, 2H), 5.67 (t, 1H, CH), 3.68 (s, 3H, OCH3), 2.95 (m, 2H, CH2), 2.38 (m, overlap, 8H, 2CH3+CH2), 1.5-2.0 (m, 4H, CH2), 1.1-1.4 (m, CH2, 20H), 0.81 (t, CH3, 3H). MS (m/e) [M$^-$] (C$_{26}$H$_{44}$NO$_6$S$^-$): calculated 498.29, observed 498.5.

Sodium 3-((((1-(4-methoxy-2,3,6-trimethylphenyl)tridecyl)oxy)carbonyl)amino) propane-1-sulfonate (7640). $^1$H NMR (d$^6$-DMSO, δ ppm): 7.13 (t, 1H, NH), 6.61 (s, 1H), 5.72 (t, 1H, CH), 3.72 (s, 3H, OCH3), 2.94 (m, 2H, CH2), 2.38 (m, overlap, 5H, CH3+CH2), 2.27 (s, 3H, CH3), 2.09 (s, 3H, CH3), 1.5-2.0 (m, 4H, CH2), 1.1-1.4 (m, CH2, 20H), 0.81 (t, CH3, 3H). MS (m/e) [M$^-$] (C$_{27}$H$_{46}$NO$_6$S$^-$): calculated 512.31, observed 512.5.

Sodium 3-((((1-(5-bromofuran-2-yl)tridecyl)oxy)carbonyl)amino)propane-1-sulfonate (7484). $^1$H NMR (d$^6$-DMSO, δ ppm): 7.25 (t, 1H, NH), 6.51 (d, 1H), 6.48 (d, 1H), 5.53 (t, 1H, CH), 2.97 (m, 2H, CH2), 2.32 (t, 2H, CH2), 1.82 (q, 2H, CH2), 1.63 (m, 2H, CH2), 1.1-1.4 (m, CH2, 20H), 0.8 (t, CH3, 3H). MS (m/e) [M$^-$] (C$_{25}$H$_{35}$BrNO$_6$S): calculated 508.14, observed 508.8.

Sodium 3-((((1-(3,4-dimethoxyphenyl)tridecyl)oxy)carbonyl)amino)propane-1-sulfonate (7486). $^1$H NMR (d$^6$-DMSO, δ ppm): 7.21 (t, 1H, NH), 6.7-7.0 (m, 3H), 5.48 (t, 1H, CH), 3.73 (m, 6H, OCH3), 2.93 (m, 2H, CH2), 2.38 (t, 2H, CH2), 1.5-1.8 (m, 4H, CH2), 1.1-1.4 (m, CH2, 20H), 0.75 (t, CH3, 3H). MS (m/e) [M$^-$] (C$_{25}$H$_{42}$NO$_7$S$^-$): calculated 500.67, observed 500.3.

Sodium 3-((((1-(4-methoxyphenyl)tridecyl)oxy)carbonyl)amino)propane-1-sulfonate (7124). $^1$H NMR (d$^6$-DMSO, δ ppm): 7.25 (d, 2H), 7.15 (t, 1H), 6.82 (d, 2H), 5.48 (t, 1H, CH), 3.73 (s, 3H, OCH3), 2.93 (m, 2H, CH2), 2.38 (t, 2H, CH2), 1.5-1.8 (m, 4H, CH2), 1.1-1.4 (m, CH2, 20H), 0.75 (t, CH3, 3H). MS (m/e) [M$^-$] (C$_{24}$H$_{40}$NO$_6$S$^-$): calculated 470.26, observed 470.3.

Sodium 3-((((1-(4-isopropoxyphenyl)tridecyl)oxy)carbonyl)amino)propane-1-sulfonate (7495). $^1$H NMR (d$^6$-DMSO, δ ppm): 7.25 (d, 2H), 7.18 (t, 1H, NH), 6.81 (d, 2H), 5.48 (t, 1H, CH), 4.61 (m, 1H, CH), 2.93 (m, 2H, CH2), 2.39 (t, 2H, CH2), 1.5-1.8 (m, 4H, CH2), 1.1-1.4 (m, CH2, 20H), 0.75 (t, CH3, 3H). MS (m/e) [M$^-$] (C$_{26}$H$_{44}$NO$_6$S$^-$): calculated 498.70, observed 498.5.

4-((((1-(4-methoxyphenyl)tridecyl)oxy)carbonyl)amino)butanoic acid (7365). $^1$H NMR (d$^6$-DMSO, δ ppm): 7.25 (d, 2H), 6.82 (d, 2H), 5.67 (t, 1H, CH), 4.85 (s, br, 1H), 3.69 (s, 3H, OCH3), 3.2 (m, 2H, CH2), 2.38 (t, 2H, CH2), 1.5-1.8 (m, 4H, CH2), 1.1-1.4 (m, CH2, 20H), 0.78 (t, CH3, 3H). MS (m/e) [M-H] (C$_{25}$H$_{41}$NO$_5$): calculated 435.3, observed 434.5.

(((1-(4-methoxyphenyl)tridecyl)oxy)carbonyl)glutamic acid (7366). $^1$H NMR (d$^6$-DMSO, δ ppm): 7.21 (d, 2H), 6.87 (d, 2H), 5.5-5.7 (m, 1H), 4.1-4.3 (m, 2H), 3.69 (s, 3H, OCH3), 1.5-1.8 (m, 4H, CH2), 1.1-1.4 (m, CH2, 20H), 0.83 (t, CH3, 3H). MS (m/e) [M$^-$] ($C_{26}H_{41}NO_7$): calculated 479.3, observed 478.5.

(((1-(4-methoxyphenyl)tridecyl)oxy)carbonyl)aspartic acid (7367). $^1$H NMR (d$^6$-DMSO, δ ppm): 7.25 (d, 2H), 6.87 (d, 2H), 5.5-5.7 (m, 1H), 4.62 (m, 1H), 3.81 (s, 3H, OCH3), 2.7-3.2 (m, 2H), 1.5-2.0 (m, 4H, CH2), 1.1-1.4 (m, CH2, 20H), 0.83 (t, CH3, 3H). MS (m/e) [M-H] ($C_{25}H_{39}NO_7$): calculated 465.27, observed 464.3.

4-((((1-(5-chlorofuran-2-yl)tridecyl)oxy)carbonyl)amino) butanoic acid (7437). $^1$H NMR (d$^6$-DMSO, δ ppm): 7.26 (t, 1H, NH), 6.52 (d, 1H), 6.43 (d, 1H), 5.55 (t, 1H, CH), 2.95 (m, 2H, CH2), 2.37 (t, 2H, CH2), 1.81 (q, 2H, CH2), 1.63 (m, 2H, CH2), 1.1-1.4 (m, CH2, 20H), 0.81 (t, CH3, 3H). MS (m/e) [M$^-$] ($C_{22}H_{36}ClNO_5$): calculated 429.23, observed 428.4.

4-((((1-(5-chlorofuran-2-yl)tridecyl)oxy)carbonyl)amino) glutamic acid (7439). $^1$H NMR (d$^6$-DMSO, δ ppm): 7.53 (t, 1H, NH), 6.53 (d, 1H), 6.44 (d, 1H), 5.55 (t, 1H, CH), 3.91 (m, 2H), 2.28 (m, 2H, CH2), 1.6-2.2 (m, 4H, CH2), 1.1-1.4 (m, CH2, 20H), 0.81 (t, CH3, 3H). MS (m/e) [M$^-$] ($C_{23}H_{36}ClNO_7$): calculated 473.22, observed 472.4.

4-((((1-(5-chlorofuran-2-yl)tridecyl)oxy)carbonyl)amino) aspartic acid (7438). $^1$H NMR (d$^6$-DMSO, δ ppm): 7.59 (t, 1H, NH), 6.53 (m, 1H), 6.44 (m, 1H), 5.55 (t, 1H, CH), 4.21 (m, 2H), 2.5-2.8 (m, 2H, CH2), 1.72 (m, 2H, CH2), 1.1-1.4 (m, CH2, 20H), 0.81 (t, CH3, 3H). MS (m/e) [M$^-$] ($C_{23}H_{36}ClNO_7$): calculated 459.22, observed 458.4.

Example 2

DNA Polymerase Inhibitor #7124 and Derivatives

To demonstrate that the thermally-labile small molecule polymerase inhibitors of the present disclosure can provide hot-start amplification, a 1.5 kb fragment of the Corynephage omega gene from plasmid DNA was amplified. When carried out using hot-start conditions, the polymerase (e.g., Taq polymerase) was inhibited at lower temperatures, but activated at the start of amplification when temperatures increased to denature the DNA (e.g., 95° C.); the amplification produced a single product approximately 1.5 kb in size. When carried out using non-hot-start conditions, the DNA polymerase was not inhibited at lower temperatures, and amplification produced a product approximately 400 bp in size (among other secondary products), and the 1.5 kb fragment was transiently present. To test the ability of the thermally-labile small molecule polymerase to inhibit DNA polymerase (e.g., Taq DNA polymerase) activity, the amplification reactions were incubated at 22° C. for 1.5 to 6 hours or longer prior to performing PCR amplification.

The amplifications were set up at room temperature. The thermally-labile small molecule polymerase inhibitor(s) were titrated (concentrations will depend on exact compound, enzyme being inhibited, detergent concentration, and other buffer conditions) into reactions. For these experiments, the following composition were used: 1× GoTaq® Colorless Flexi Buffer, 2.5 mM MgCl$_2$, 200 μM each dNTP, 0.4 μM each primer, 0.025 U/μl GoTaq® DNA Polymerase, 500 pg plasmid DNA and nuclease-free water to bring it to a 25 μl reaction. "No small molecule inhibitor", "no template control" (NTC), and "positive hot-start" (using GoTaq® DNA polymerase with an antibody-mediated hot-start) control reactions were assembled. The reactions were inserted into a room temperature thermal cycler, and the following cycling protocol was used: 1 cycle (22° C. for 1.5 to 6 hours, 95° C. for 2 minutes), 30 cycles (93° C. for 15 seconds, 54° C. for 30 seconds, 72° C. for 1 minute), 1 cycle (72° C. for 5 minutes), and 4° C. soak. Once cycling was complete, PCR products were separated and visualized on a 1% agarose gel with ethidium bromide staining and UV-light illumination. A camera was used to record the image of the gel.

As expected, hot-start control reactions (using antibody-mediated hot-start DNA polymerase) and reactions with small molecule inhibitor(s) exhibiting hot-start ability amplified a single 1.5 kb product. In the "no small molecule inhibitor control" reactions and reactions with small molecule inhibitor(s) not exhibiting hot-start ability, a 400 bp product was amplified (Other secondary products and a 1.5 kb product may or may not be present)). In the "no template" control, no amplification occurred.

FIGS. 1A-1B include representative images of agarose gels used to evaluate the amplification products of various hot-start PCR reactions performed with and without one of two different polymerase inhibitors of the present disclosure (compound #7124 in FIG. 1A; compound #7261 in FIG. 1B). FIG. 1A includes hot-start PCR amplification results using compound #7124 at the various concentrations listed. As demonstrated, the use of compound #7124 prevented non-specific DNA amplification (~400 kb product) while facilitating amplification of the desired DNA target (~1.5 kb). Although exact concentrations will vary depending on specific reaction conditions and reagents, use of compound #7124 at a concentration ranging from about 100 μM to about 150 μM facilitated was effective, and specific amplification of the desired DNA target was achieved.

FIG. 3 includes a representative table of the results of various hot-start PCR reactions (amplifying the 1.5 kb fragment of the Corynephage omega gene target from plasmid DNA) performed with different polymerase inhibitors that are derivatives of compound #7124 (i.e. compound #7489 and compound #7490). As demonstrated, the use of compound #7489 prevented non-specific DNA amplification and facilitated specific amplification of the desired DNA target at concentrations ranging from about 75 μM to about 175 μM. The use of compound #7490 prevented non-specific DNA amplification and facilitated specific amplification of the desired DNA target at concentrations ranging from about 100 μM to about 125 μM.

Figure 4:
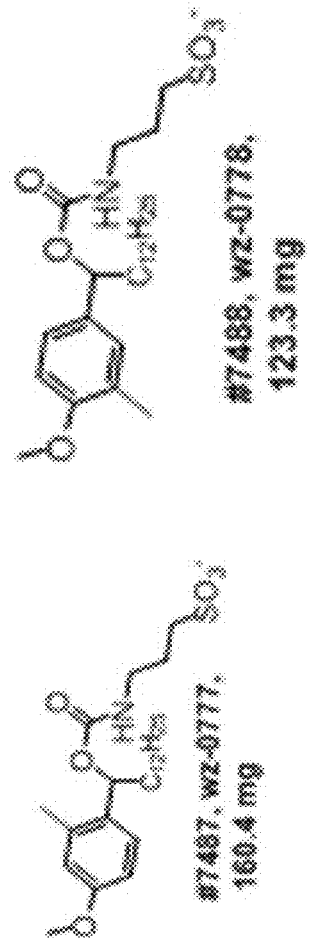
FIG. 4 includes a representative table of the results of various hot-start PCR reactions performed with different polymerase inhibitors (i.e., compound #7487 and compound #7488; variations of compound #7124).

FIG. 4 includes a representative table of the results of various hot-start PCR reactions (amplifying the 1.5 kb fragment of the Corynephage omega gene target from plasmid DNA) performed with different polymerase inhibitors that are derivatives of compound #7124 (i.e. compound #7487 and compound #7488). As demonstrated, the use of compound #7487 prevented non-specific DNA amplification and facilitated specific amplification of the desired DNA target at concentrations ranging from about 75 μM to about 150 μM. The use of compound #7488 prevented non-specific DNA amplification and facilitated specific amplification of the desired DNA target at concentrations ranging from about 75 μM to about 100 μM.

Figure 5:
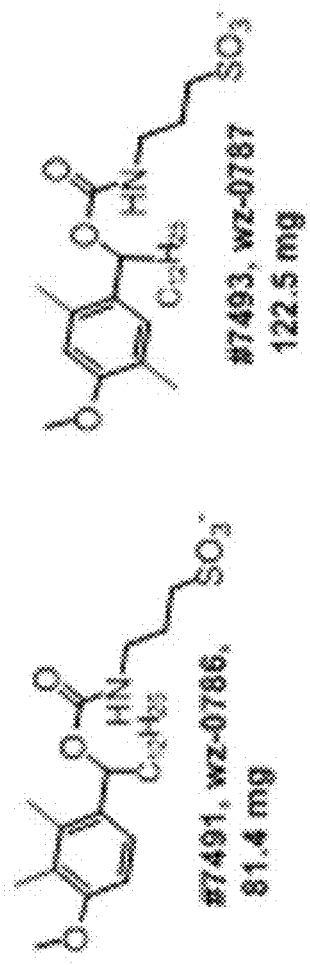
FIG. 5 includes a representative table of the results of various hot-start PCR reactions performed with different polymerase inhibitors (i.e., compound #7491 and compound #7493; variations of compound #7124).

FIG. 5 includes a representative table of the results of various hot-start PCR reactions (amplifying the 1.5 kb fragment of the Corynephage omega gene target from plasmid DNA) performed with different polymerase inhibitors that are derivatives of compound #7124 (i.e. compound #7491 and compound #7493). As demonstrated, the use of compound #7491 prevented non-specific DNA amplification and facilitated specific amplification of the desired DNA target at concentrations ranging from about 75 μM to about 125 μM. The use of compound #7493 prevented non-specific DNA amplification and facilitated specific amplification of the desired DNA target at concentrations ranging from about 100 μM to about 125 μM.

Figure 6:
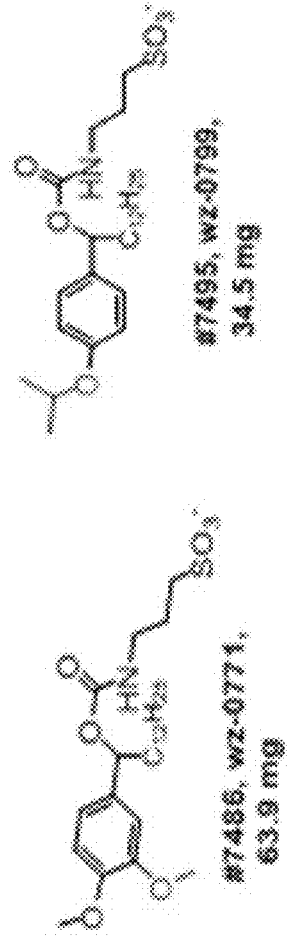
FIG. 6 includes a representative table of the results of various hot-start PCR reactions performed with different polymerase inhibitors (i.e., compound #7486 and compound #7495; variations of compound #7124).

FIG. 6 includes a representative table of the results of various hot-start PCR reactions (amplifying the 1.5 kb fragment of the Corynephage omega gene target from plasmid DNA) performed with different polymerase inhibitors that are derivatives of compound #7124 (i.e. compound #7486 and compound #7495). As demonstrated, the use of compound #7486 prevented non-specific DNA amplification and facilitated specific amplification of the desired DNA target at concentrations ranging from about 125 μM to about 175 μM. The use of compound #7495 prevented non-specific DNA amplification and facilitated specific amplification of the desired DNA target at concentrations ranging from about 50 μM to about 75 μM.

With respect to FIGS. 2-6, "No HS" designates reactions that did not prevent amplification of non-specific products; "HS" designates reactions that prevented amplification of non-specific products and facilitated amplification of specific products; and "No Amp" designates no amplification of specific or non-specific products. Amplification yield assessment is provided in parentheses as: "++" (good yield similar to hot-start control); "+" (moderate yield), and "low" (low yield).

Example 3

DNA Polymerase Inhibitor #7261 and Derivatives

The same methods described in Example 2 above were used to test the activity of DNA polymerase inhibitor #7261 and its derivatives. FIG. 1B includes hot-start PCR amplification results (amplifying the 1.5 kb fragment of the Corynephage omega gene target from plasmid DNA) using compound #7261 at the various concentrations listed. As demonstrated, the use of compound #7261 prevented non-specific DNA amplification (~400 kb product) while facilitating amplification of the desired DNA target (~1.5 kb). Although exact concentrations will vary depending on specific reaction conditions and reagents, use of compound #7261 at a concentration ranging from about 75 μM to about 100 μM facilitated effective and specific amplification of the desired DNA target.

FIG. 2 includes a representative table of the results of various hot-start PCR reactions (amplifying the 1.5 kb fragment of the Corynephage omega gene target from plasmid DNA) performed with different polymerase inhibitors that are derivatives of compound #7261 (i.e., compound #7437, compound #7438, and compound #7439). As demonstrated, the use of compound #7437 prevented non-specific DNA amplification and facilitated specific amplification of the desired DNA target at concentrations ranging from about 100 μM to about 150 μM. The use of compound #7438 prevented non-specific DNA amplification and facilitated specific amplification of the desired DNA target at concentrations ranging from about 25 μM to about 200 μM. The use of compound #7439 prevented non-specific DNA amplification and facilitated specific amplification of the desired DNA target at concentrations ranging from about 50 μM to about 225 μM. In particular, potency of DNA polymerase #7261 inhibitors was enhanced from about 75 μM to from about 25 μM to about 150 μM or greater for #7438 and #7439.

Example 4

Evaluation of Polymerase Inactivation at Different Temperatures

Activity assays were used to test the concentrations of small molecule polymerase inhibitors in specific reaction conditions to determine inhibition efficacy. Corresponding $IC_{50}$ values were also determined for the compounds. Activity assays were also used to test the temperatures or temperature ranges at which the reactions are inhibited by the compounds.

Exemplary activity assays can be carried out according to a variety of methods. For example, a DNA polymerase activity assay monitoring radioactive incorporation where "activated" calf thymus or salmon sperm DNA is used as the DNA substrate. Along with the DNA substrate, the reactions minimally contain a buffer (e.g., GoTaq® buffer), magnesium, dNTPs, and polymerase. Reactions were stopped, and DNA was precipitated by ice-cold TCA (tricholoracetic acid), incubated on ice for at least 10 minutes, filtered using GF/C filters, and radioactive incorporation in precipitable DNA (on filter) measured by scintillation counting. (See, e.g., Apospian & Kornberg. (1962) JBC 237: 519-525; Chien et al. (1976) J. Bact. 127: 1550-1557.)

A primer extension DNA polymerase activity assay monitoring radioactive incorporation, wherein single-stranded DNA (e.g., M13) and primer substrate was used as the DNA substrate. The primer and template were annealed, and reactions minimally contain buffer (e.g., GoTaq® buffer), magnesium, dNTPs, and polymerase. Reactions were stopped, and DNA precipitated by ice-cold TCA, incubated on ice for at least 10 minutes, filtered using GF/C filters, and radioactive incorporation in precipitable DNA on filter measured by scintillation counting. (See, e.g., Longley & Mosbaugh. (1991) Biochemistry 30: 2655-2664.)

Figure 7:
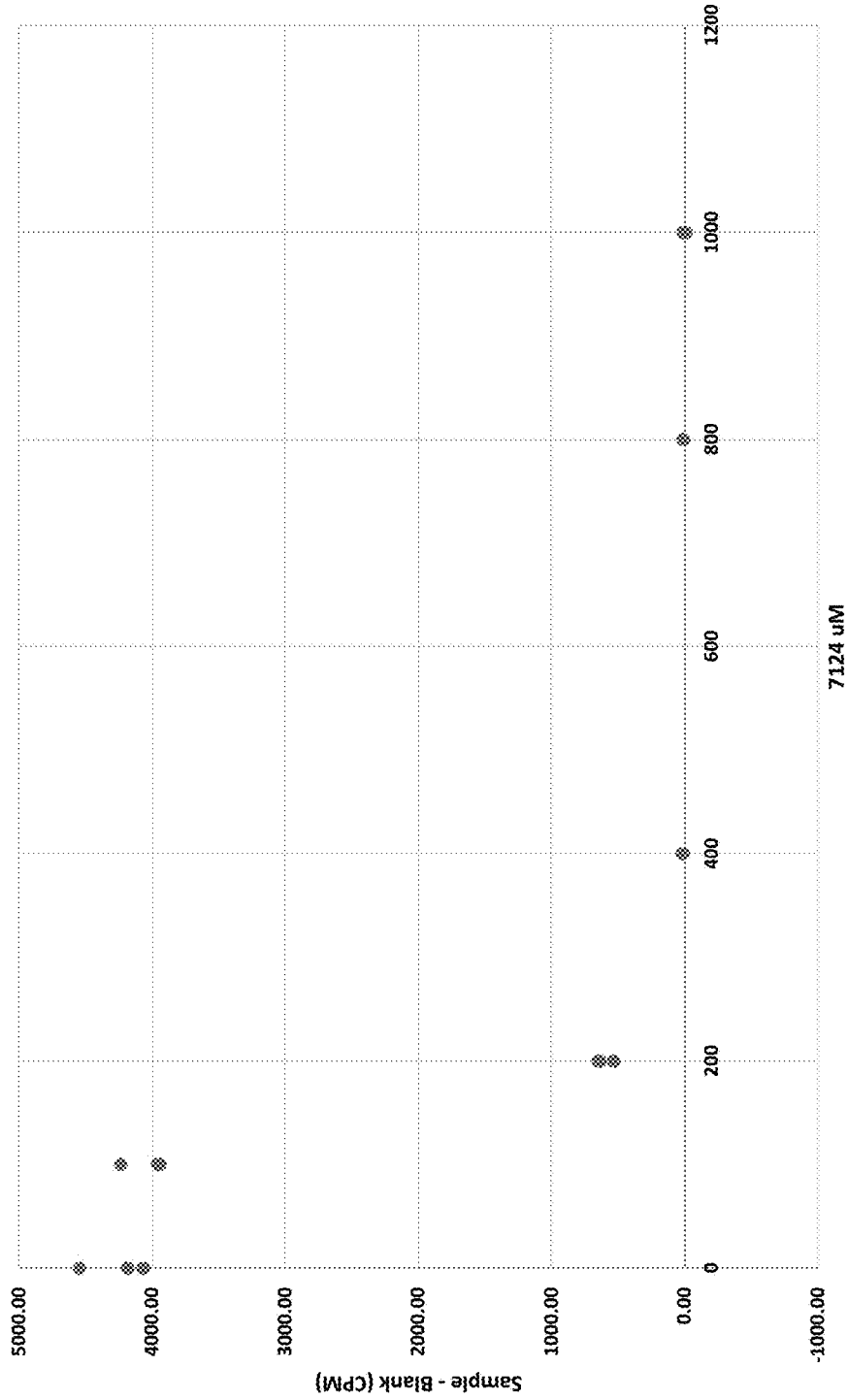
FIG. 7 includes a representative graph of the results of Taq DNA Polymerase activity at 22° C. for a titration of a polymerase inhibitor (i.e. compound #7124), which can be used to estimate the $IC_{50}$.

FIG. 7 includes a representation of a polymerase activity assay carried out at 22° C., where an inhibitor (i.e. compound #7124) is titrated. FIG. 7 is an example of an activity assay where $IC_{50}$ can be determined. Compound 7124 did not inhibit Taq DNA Polymerase at low concentrations; however, as concentration increased, inhibition begins and ultimately reaches 100% inhibition. From this graph, an $IC_{50}$ was calculated to be about 150 μM. Activated calf thymus DNA activity assay was used in these experiments. Assays similar to this can be used to determine other conditions under which enzyme inhibition occurs (e.g., temperatures, buffer conditions, and different DNA polymerases).

FIG. 8 includes a representative table of results of $IC_{50}$ values for different polymerase inhibitors when incubated at 22° C. (i.e. compound #7124, compound #7126, compound #7127, compound #7123, compound #7125, compound #6966, and SDS). FIG. 8 is an example of $IC_{50}$ information for a variety of compounds. To determine the $IC_{50}$ values, experiments similar to those done in FIG. 7 were performed. Activated calf thymus DNA method was used for these experiments.

Example 5

Evaluation of Activation of Enzymes by Temperature

To test activation temperatures and times to determine when activity is restored, activity assay reactions can be assembled with and without small molecule polymerase inhibitors (as described further above). Reactions start at low temperature (e.g., 22° C. or 37° C.) for a period of time. Temperatures of the reactions can be increased to a high temperature (e.g., >90° C.) and incubated for a given amount of time to allow for enzyme activation. The reaction temperatures can be decreased to 68-79° C. and incubated for 15 minutes. Reactions can be stopped, samples processed, and activity calculated to determine the amount of enzyme activity that can be recovered.

In accordance with these methods, PCR can be used to test activation of polymerase enzymes and to determine the most effective conditions for each small molecule inhibitor, for example, by adjusting the temperature and time of the initial denaturation step (e.g., Corynebacterium omega gene, or a target from human genomic DNA).

Example 6

Real-Time Inhibition and Activation Conditions

In accordance with the methods of the present disclosure, experiments can also be conducted using a real-time extension rate activity assay method to measure nucleotide incorporation of a DNA polymerase. For example, a primer extension assay can include a process by which extension is monitored on a real-time PCR instrument using non-covalent DNA dyes such as BRYT™ Green or SYBR® Green and an oligonucleotide DNA substrate. (See, e.g., Montgomery & Wittwer (2014), Clinical Chemistry 60(2):334-340). Activity assay reactions can be assembled with and without a small molecule polymerase inhibitor. The reactions minimally include buffer (e.g., GoTaq® buffer), magnesium, dNTPs, DNA substrate, and polymerase.

In one embodiment of the assay, the reactions can be monitored to determine the temperature at which the enzyme starts to be activated. Reactions can be incubated at a low temperature (e.g., 22° C., 37° C., 55° C., etc.) to a high temperature (68° C., 72° C., 79° C., etc.) for a given period of time while measuring extension rate to assess inhibition of the polymerase.

In another embodiment of the assay, the temperature and times needed for activation can be investigated. Reactions can be incubated at a low temperature (e.g., 22° C. or 37° C.) for a period of time while monitoring the activity. Temperatures of the reactions can be increased to a high temperature (e.g., >90° C.) and incubated for a given amount of time to try to activate the enzyme. The reaction temperatures can then be decreased to 68-79° C. and incubated as in the standard activity assay to measure the enzyme activity recovered.

Example 7

Evaluation of Compounds for Inhibition of Nuclease Activity Associated with DNA Polymerases Many DNA polymerases have associated domains with nuclease activity (e.g., Taq has a 5' nuclease and Pfu has a 3' to 5' proof-reading nuclease). Both the 5' nuclease and the 3' to 5' nuclease activities can be problematic for PCR. For example, the 5' nuclease activity can remove dyes on the 5' end of primers if the appropriate structure is formed with the DNA in the reaction during set up. Also, for example, the 3' to 5' nuclease activity can degrade primers and template in the reaction during setup. These troublesome side reactions can also be inhibited by the small molecule polymerase inhibitors of the present disclosure.

To study the ability of the small molecule polymerase inhibitors of the present disclosure to inhibit nuclease activities, a 5' nuclease activity assay (for an enzyme such as Taq) can be performed using a 5' fluorescently dye-labeled bifurcated duplex DNA substrate. (See, e.g., Lyamichev et al. (1993) Science 260: 778-783; Lyamichev (1999) PNAS 96:6143-6148; Ceska & Sayers (1998) TIBS: 331-336). The DNA substrate can be annealed and combined with reaction components including buffer (e.g., GoTaq® buffer), magnesium, and a nuclease or a polymerase with a nuclease domain. Reaction can be stopped with EDTA and run on a capillary electrophoresis instrument to determine amount of cut and uncut DNA substrate.

Additionally, a 3' to 5' exonuclease activity assay (for a proofreading polymerase such as Pfu) can be performed using a 3'-radiolabeled duplexed DNA as a substrate. The DNA substrate can be combined with reaction components including buffer (e.g., GoTaq® buffer), magnesium, and a nuclease or a polymerase with a nuclease domain. Reactions can be stopped by EDTA, and DNA can be precipitated by ice-cold TCA and incubated on ice for at least 10 minutes. Precipitable DNA can be pelleted by centrifugation and released non-precipitable DNA from radioactively labeled 3' end can be measured by scintillation counting. (See, e.g., Chase & Richardson. (1974) JBC 249: 4545-4552; Sambrook et al. (1989) Molecular Cloning: A Laboratory Manual (2nd Edition), pp. 10.51-52).

Example 8

Variations of Methods

As would be appreciated by one of ordinary skill in the art based on the present disclosure, the small molecule polymerase inhibitors of the present disclosure can be used to inhibit the activity of other enzymes, or activities of associated domains, such as, but not limited to, ligase, reverse transcriptase, and RNase H. Activity of these enzymes can be investigated in the context of PCR, rtPCR, or other DNA/RNA amplification methods.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

What is claimed is:

1. A compound of formula (I):

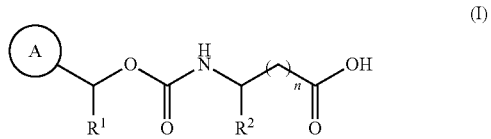

or a salt thereof, wherein:

A is selected from aryl, heteroaryl, and heterocyclyl, each of which may be optionally substituted with 1, 2, or 3 substituents;

$R^1$ is $C_6$-$C_{20}$ alkyl;

$R^2$ is selected from hydrogen and —COOH; and n is 1 or 2.

2. The compound of claim 1, or a salt thereof, wherein A is phenyl that is unsubstituted or substituted with 1, 2, or 3 substituents independently selected from $C_1$-$C_4$ alkyl, $C_1$-$C_4$ alkoxy, and halo.

3. The compound of claim 1, or a salt thereof, wherein A is a 5- or 6-membered monocyclic heteroaryl that is unsubstituted or substituted with 1, 2, or 3 substituents independently selected from $C_1$-$C_4$ alkyl, $C_1$-$C_4$ alkoxy, and halo.

4. The compound of claim 1, or a salt thereof, wherein A is a bicyclic heterocyclyl group that is unsubstituted.

5. The compound of claim 1, or a salt thereof, wherein $R^1$ is $C_8$-$C_{14}$ alkyl.

6. The compound of claim 1, wherein the compound is selected from:

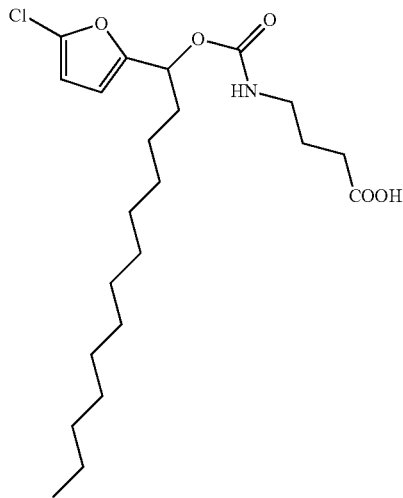

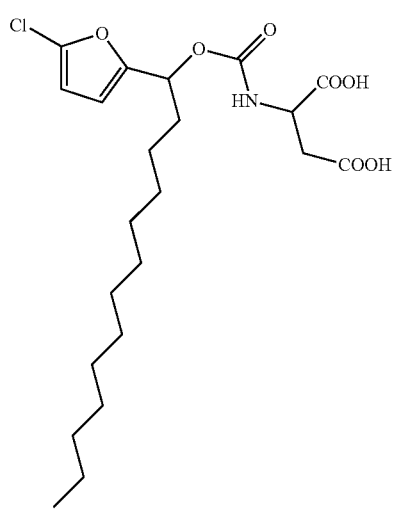

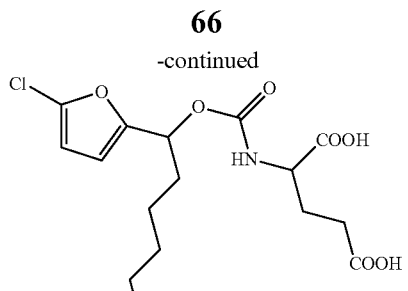

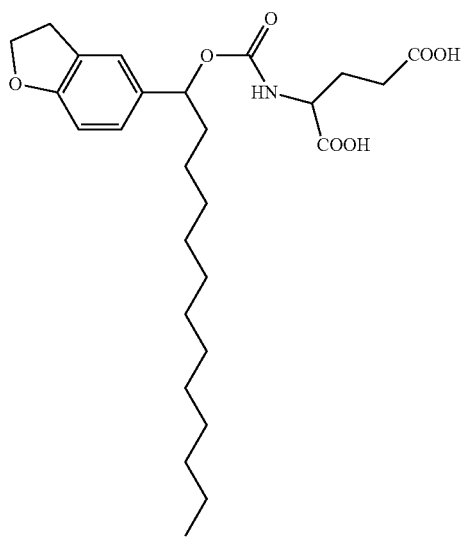

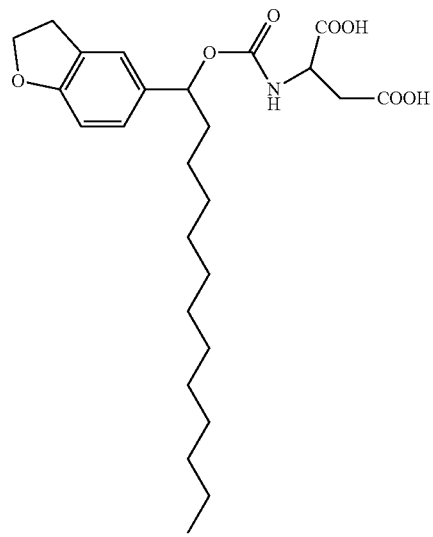

67
-continued

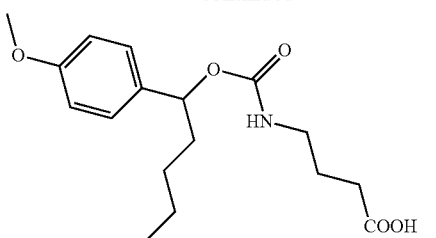

and

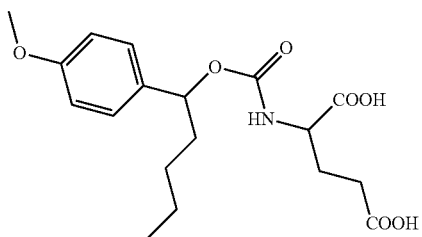

68
-continued

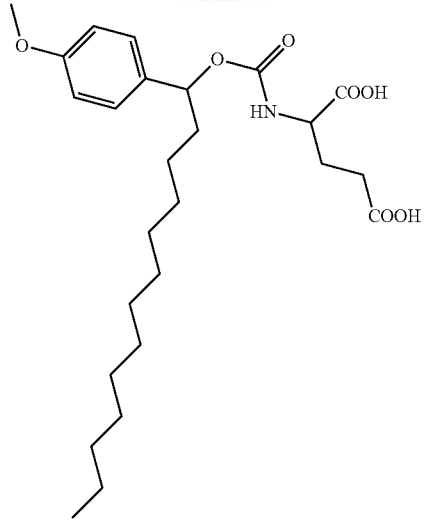

or a salt thereof.

7. A composition comprising a compound claim 1 or a salt thereof, and a thermostable DNA polymerase.

8. The composition of claim 7, wherein the thermostable DNA polymerase is selected from the group consisting of: Taq, Tca, Tfu, Tbr, Tth, Tih, Tfi, Tli, Tfl, Pfu, Pwo, KOD, Tma, Tne, Bst, Pho, Sac, Sso, ES4, or a mutant, variant or derivative thereof.

9. The composition of claim 7, wherein the compound is bound to the DNA polymerase and inhibits the activity of the DNA polymerase.

10. The composition of claim 7, further comprising one or more nucleic acid amplification reagents selected from the group consisting of: deoxynucleotide triphosphates, buffer, a magnesium salt, an oligonucleotide primer, and a nucleic acid template.

11. A composition comprising a compound of claim 1 or a salt thereof, and one or more nucleic acid amplification reagents selected from the group consisting of: a polymerase, deoxynucleotide triphosphates, buffer, a magnesium salt, an oligonucleotide primer, and a nucleic acid template.

* * * * *